United States Patent
Henry et al.

(10) Patent No.: US 12,325,849 B2
(45) Date of Patent: Jun. 10, 2025

(54) APPARATUS AND A METHOD FOR THE USE OF PULSED ELECTROMAGNETIC FIELD TO CHANGE THE CONDITION OF A PRODUCT AND/OR THE GENERATION OF SAID PRODUCT

(71) Applicant: St Andrews Pharmaceutical Technology Ltd., Henley-on-Thames (GB)

(72) Inventors: William John Henry, St. Andrews (GB); Christopher Taylor, Maidenhead (GB)

(73) Assignee: St. Andrews Pharmceutical Technology Ltd., Henley-on-Thames (GB)

( * ) Notice: Subject to any disclaimer, the term of this patent is extended or adjusted under 35 U.S.C. 154(b) by 1040 days.

(21) Appl. No.: 16/972,178

(22) PCT Filed: Jun. 7, 2019

(86) PCT No.: PCT/GB2019/051584
§ 371 (c)(1),
(2) Date: Dec. 4, 2020

(87) PCT Pub. No.: WO2019/234442
PCT Pub. Date: Dec. 12, 2019

(65) Prior Publication Data
US 2021/0189317 A1 Jun. 24, 2021

(30) Foreign Application Priority Data

| Jun. 7, 2018 | (GB) | 1809355 |
| Aug. 20, 2018 | (GB) | 1813537 |
| Dec. 6, 2018 | (GB) | 1819886 |

(51) Int. Cl.
*C12M 1/42* (2006.01)
*C12H 1/16* (2006.01)

(52) U.S. Cl.
CPC ............. *C12M 35/04* (2013.01); *C12H 1/165* (2013.01); *C12M 35/02* (2013.01)

(58) Field of Classification Search
None
See application file for complete search history.

(56) References Cited

U.S. PATENT DOCUMENTS 5,288,471 A * 2/1994 Corner .................. A23C 3/07
426/244
5,860,353 A 1/1999 Ceccarani
(Continued)

FOREIGN PATENT DOCUMENTS

BR 112020024928 A2 3/2021
CA 3102911 A1 12/2019
(Continued)

OTHER PUBLICATIONS

Foreign Communication from a Related Counterpart Application, International Search Report and Written Opinion dated Sep. 2, 2019, International Application No. PCT/GB2019/051584 filed on Jun. 7, 2019.
(Continued)

*Primary Examiner* — Brian R Gordon
(74) *Attorney, Agent, or Firm* — Conley Rose, P.C.; Michael W. Piper; Elexis A. Jones

(57) ABSTRACT

The invention relates to apparatus and a method to allow the application of an electromagnetic field to a product for a period of time to alter a condition of the product. The condition change may be to speed up an occurring process and/or change quality of the experience of subsequent use of the product. The apparatus includes a support and a con-
(Continued)

tainer in which the said product is located. The support includes one or more modules for generation of a pulsed electromagnetic field (PEMF) and the support and hence modules are connected to control means to control the generation of the PEMF and are positionable with respect to the said product so as to allow the product to be exposed to the generated PEMF.

15 Claims, 26 Drawing Sheets

(56) References Cited

U.S. PATENT DOCUMENTS

| | | | |
|---|---|---|---|
| 8,039,031 B2 | 10/2011 | Baianu et al. | |
| 11,555,170 B2* | 1/2023 | Flynn | C12M 21/02 |
| 2005/0251229 A1* | 11/2005 | Pilla | A61N 1/40 607/86 |
| 2006/0024822 A1 | 2/2006 | Chang et al. | |
| 2007/0009382 A1* | 1/2007 | Bedingham | G01N 21/6428 422/63 |
| 2008/0229849 A1* | 9/2008 | Doebler | G01N 21/6428 73/864.91 |
| 2009/0146061 A1* | 6/2009 | Manneschi | G01N 27/023 250/339.12 |
| 2010/0055756 A1* | 3/2010 | Spooner | C12M 35/02 435/285.1 |
| 2010/0322911 A1* | 12/2010 | Lu | A61P 43/00 424/93.73 |
| 2011/0207209 A1* | 8/2011 | Hammons | C12M 23/42 435/303.1 |
| 2012/0191163 A1* | 7/2012 | Yelin | A61K 47/6923 977/773 |
| 2013/0267020 A1* | 10/2013 | Goodwin | C12M 35/04 435/298.1 |
| 2014/0302482 A1* | 10/2014 | Dietz | A01N 1/0294 435/307.1 |
| 2015/0144793 A1* | 5/2015 | Whalley | A61M 5/1689 250/357.1 |
| 2015/0185143 A1* | 7/2015 | Manneschi | G01N 21/359 250/339.12 |
| 2017/0138847 A1* | 5/2017 | Pate | G01J 3/42 |
| 2017/0254738 A1* | 9/2017 | Vacca | G01N 15/1459 |
| 2018/0010149 A1* | 1/2018 | Mazur | C12M 35/02 |
| 2018/0064881 A1* | 3/2018 | Whalley | A61M 5/31535 |
| 2018/0142193 A1* | 5/2018 | Suzuki | C12M 23/20 |
| 2018/0178261 A1* | 6/2018 | Perkins | B08B 7/02 |
| 2018/0306027 A1* | 10/2018 | Sherman | G01N 33/24 |
| 2019/0106669 A1* | 4/2019 | Kim | C12M 27/16 |
| 2019/0309241 A1* | 10/2019 | Ott | C12N 1/12 |
| 2020/0325432 A1* | 10/2020 | Matsumoto | C12M 23/22 |
| 2021/0189317 A1 | 6/2021 | Henry et al. | |

FOREIGN PATENT DOCUMENTS

| | | |
|---|---|---|
| CN | 102595914 A | 7/2012 |
| CN | 113015788 A | 6/2021 |
| JP | 2021526852 A | 10/2021 |
| KR | 1020100096685 A | 9/2010 |
| MX | 2020013257 A | 5/2021 |
| WO | 2010101461 A1 | 9/2010 |
| WO | 2019106392 A1 | 6/2019 |
| WO | 2019234442 A1 | 12/2019 |

OTHER PUBLICATIONS

Foreign Communication from a Related Counterpart Application, United Arab Emirates Office Action Summary, United Arab Emirates Application No. P6001733/2020 filed on Dec. 7, 2020.
Foreign Communication from a Related Counterpart Application, United Arab Emirates Search Report, United Arab Emirates Application No. P6001733/2020 filed on Dec. 7, 2020.
Foreign Communication from a Related Counterpart Application, Brazilian Search Report and Written Opinion dated Jun. 19, 2023, Brazilian Application No. 11 2020 024928-9 filed on Jun. 7, 2019.
Foreign Communication from a Related Counterpart Application, Israeli Notice Before Acceptance for Patent Application, Israeli Application No. 279234 dated Dec. 6, 2020.
Foreign Communication from a Related Counterpart Application, Indian Examination Report dated Sep. 12, 2022, Indian Application No. 202117000672 filed on Jan. 7, 2021.
Foreign Communication from a Related Counterpart Application, Chinese First Office Action dated Sep. 28, 2023, Chinese Application No. 201980047245.0 filed on Jun. 7, 2019.
Foreign Communication from a Related Counterpart Application, Chinese Second Office Action dated May 31, 2024, Chinese Application No. 201980047245.0 filed on Jun. 7, 2019.
Foreign Communication from a Related Counterpart Application, Saudi Arabian Examination Report, Saudi Arabian Application No. 520420725 filed on Jun. 7, 2019.
Foreign Communication from a Related Counterpart Application, Kuwait Examination Report, Kuwait Application No. KW/P/2020/418 filed on Dec. 7, 2020.
Foreign Communication from a Related Counterpart Application, Bahrain Substantive Examination Report dated Jun. 23, 2024, Bahrain Application No. 20200229, filed Dec. 7, 2020.
Foreign Communication from a Related Counterpart Application, Japanese Decision of Refusal dated Mar. 5, 2024, Japanese Application No. 2021-517921.
Foreign Communication from a Related Counterpart Application, Japanese Notification of Reasons for Refusal dated Jul. 11, 2023, Japanese Application No. 2021-517921.
Foreign Communication from a Related Counterpart Application, European Exam Report dated Jul. 13, 2023, European Application No. 19730903.2 filed on Jun. 7, 2019.
Foreign Communication from a Related Counterpart Application, Mexican Examination Report dated May 17, 2024, Mexican Application No. MX/a/2020/013257 filed on Jun. 7, 2019.
Foreign Communication from a Related Counterpart Application, Australian Exam Report dated Feb. 13, 2025, Australian Application No. 19730903.2 filed on Jun. 7, 2019.
Mattar et al., "S. cerevisiae fermentation activity after moderate pulsed electric field pretreatments", Bioelectrochemistry, vol. 103, Jun. 2015, pp. 92-97.
METI/Ministry of Economy, Trade and Industry, "What is an electromagnetic field?", https://www.meti.go.jp/policy/safety_security/industrial_safety/sangyo/electric/detail/e_health/what_denjikai.html.

* cited by examiner

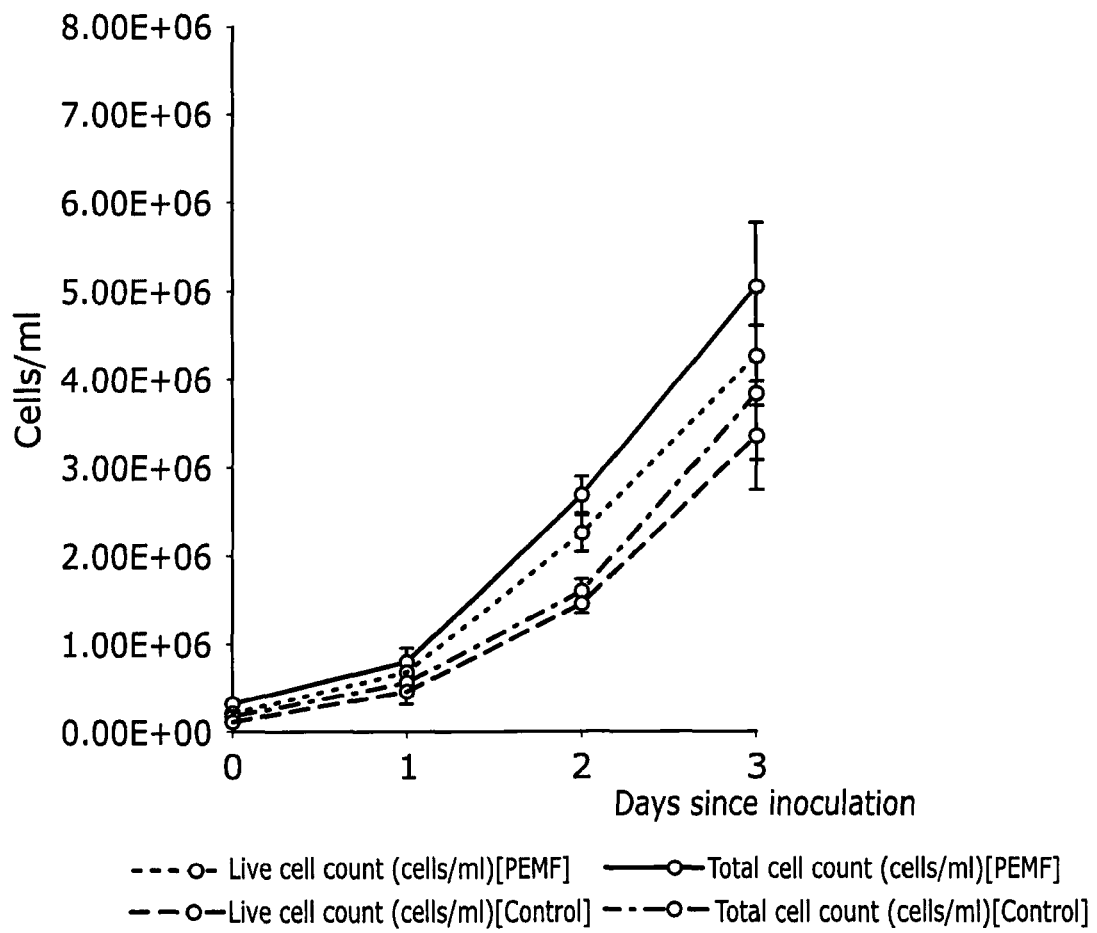
Figure 30 The average total and live cell counts in the control and PEMF-exposed cultures.

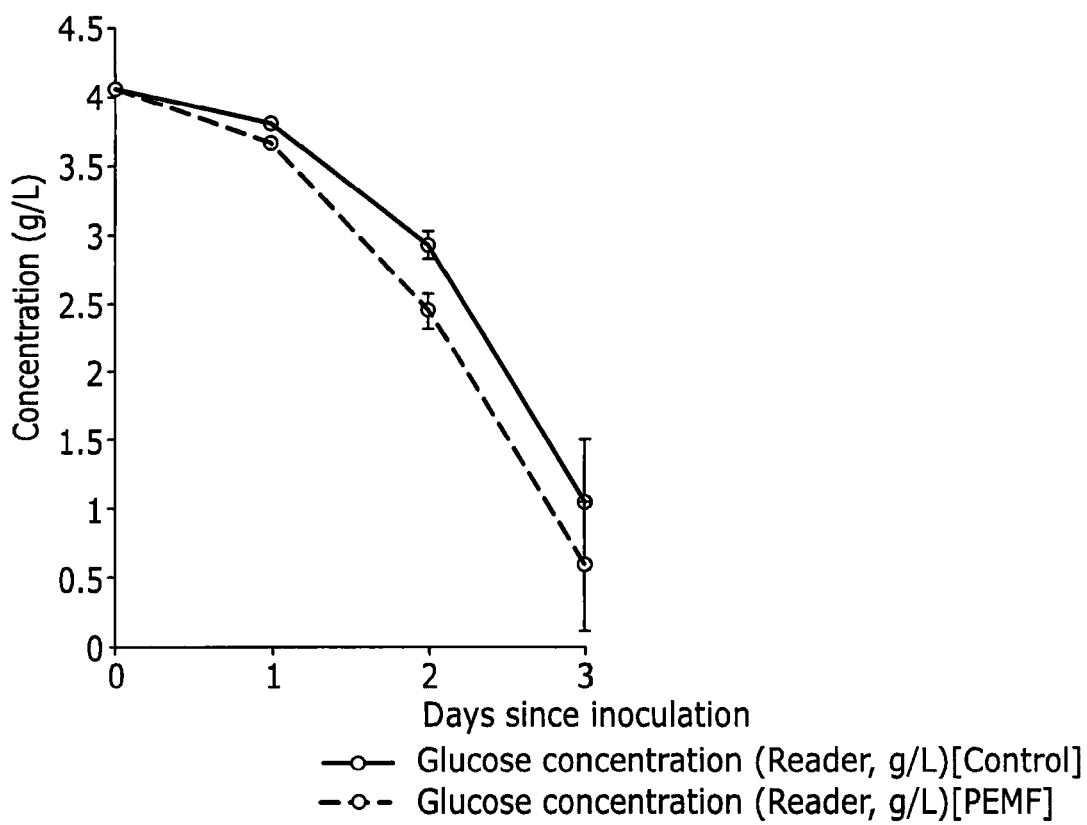
Figure 31  The average glucose concentration (g/L) in the control and PEMF-exposed cultures.
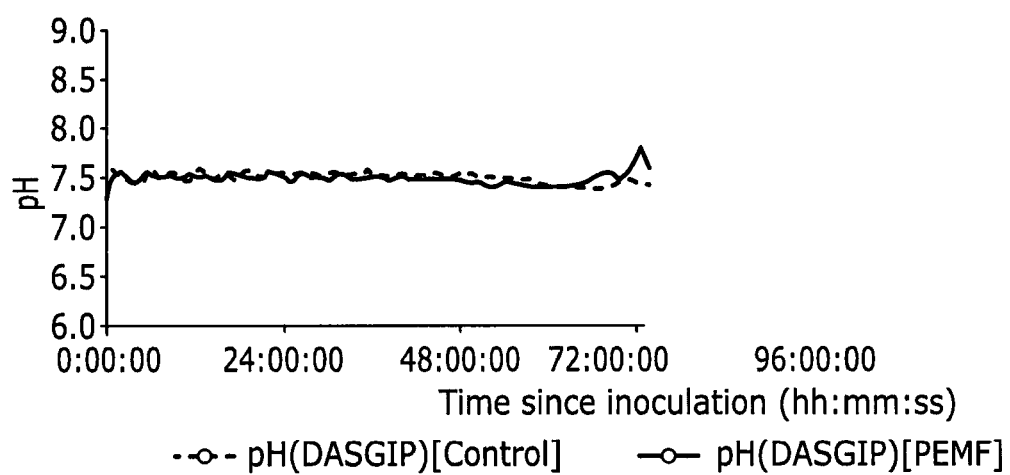
Figure 32  The average online (DASGIP) pH in the control and PEMF-exposed cultures.

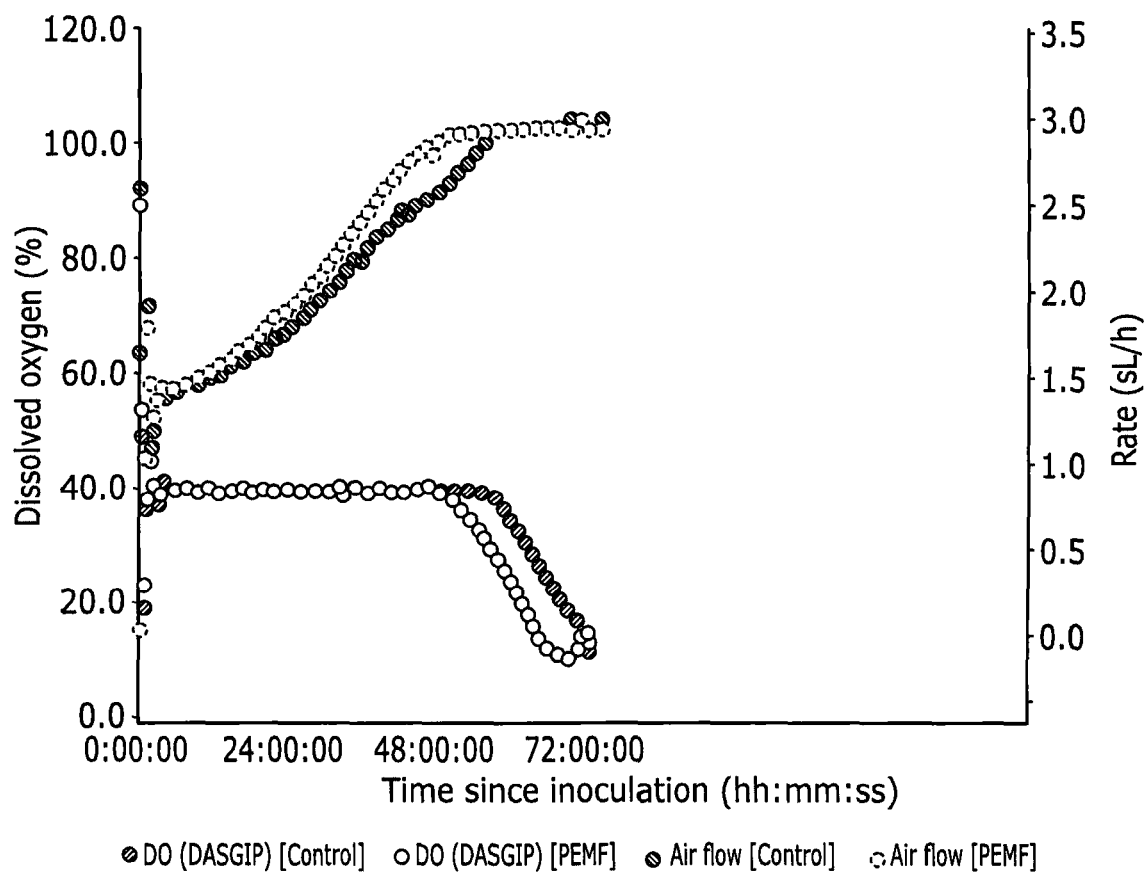
Figure 33 Average dissolved oxygen (%) and air flow(sL/h) in the control and PEMF-exposed cultures.

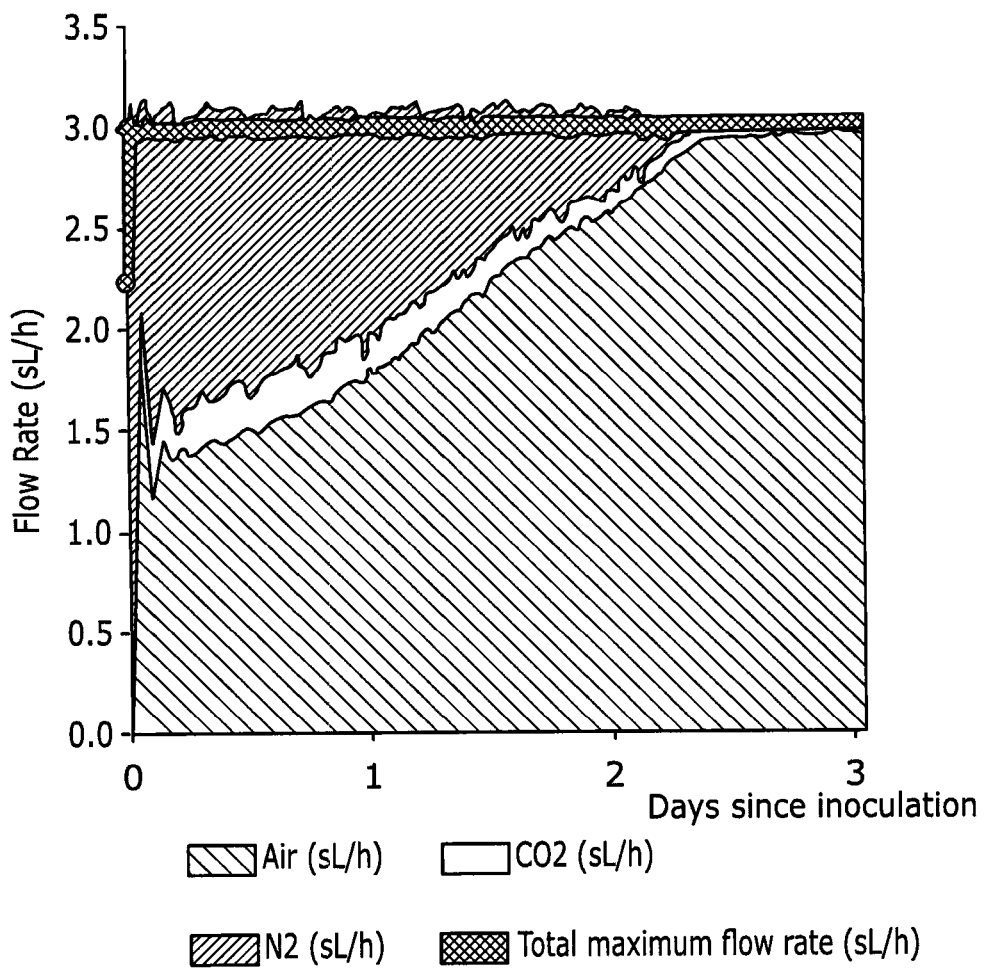
Figure 34  Total maximum gas, air, nitrogen ($n_2$) and carbon dioxide ($CO_2$) flow rates (sL/h) in the PEMF-exposed culture over 3 days of growth

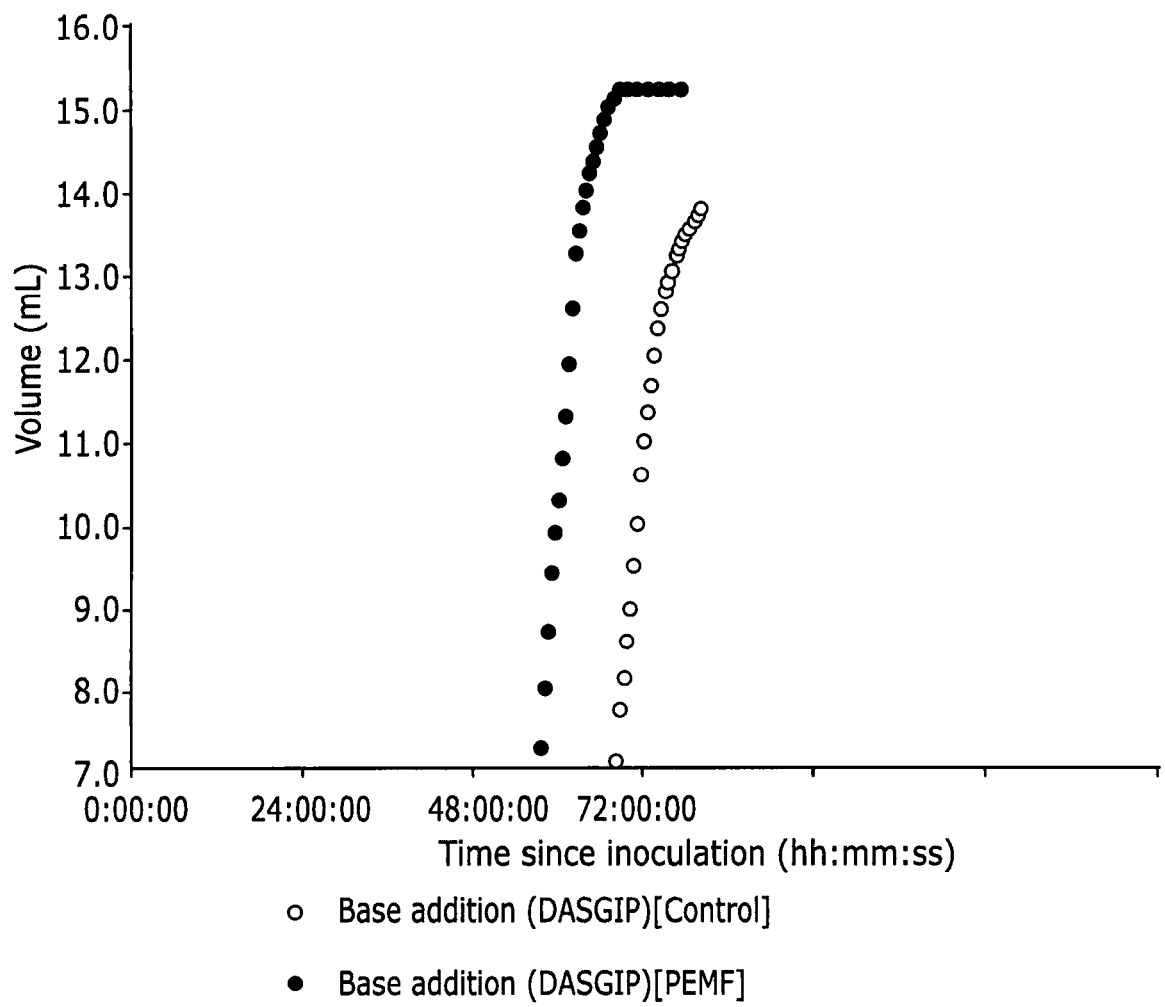
Figure 35  The average total base addition (mL) over the experimental run in the control and PEMF-exposed cultures.

APPARATUS AND A METHOD FOR THE USE OF PULSED ELECTROMAGNETIC FIELD TO CHANGE THE CONDITION OF A PRODUCT AND/OR THE GENERATION OF SAID PRODUCT

CROSS-REFERENCE TO RELATED APPLICATIONS

This United States Application is the National Phase of PCT Application No. PCT/GB2019/051584 filed 7 Jun. 2019, which claims priority to British Patent Applications No. 1809355.9 filed 7 Jun. 2018 and No. 1813537.6 filed 20 Aug. 2018 and No. 1819886.1 filed 6 Dec. 2018, each of which is incorporated herein by reference.

STATEMENT REGARDING FEDERALLY SPONSORED RESEARCH OR DEVELOPMENT

Not applicable.

REFERENCE TO A MICROFICHE APPENDIX

Not applicable.

SUMMARY

The invention to which this application relates is the application of a pulsed electromagnetic field (PEMF), (which can also be referred to as Digital sequences of Electromagnetism) to provide a change in the condition of a product and, more specifically, to change any of the metabolic productivity of biosystems such as fermentation and cell-culture bio systems and/or increase the production rate of such systems.

In the field of microbial cultures, these have been exploited for many years to produce food and drink of many types for human or animal consumption. For example, the process of fermentation of yeast (*Saccharomyces* species) is a key part of the production process for beer, wine and leavened bread. The development of this form of food manufacture was originally based on chance discoveries of natural cultures that were subsequently adopted in the production process. Thereafter, increased knowledge of the management of fermented product production has meant that development has proceeded, but still primarily on a 'trial and error' basis and relating to observations of the production processes used and then learning from mistakes made.

More recently, the development process has become more regulated and scientific but it can be argued that much of the scientific progress is in relation to the avoidance of spoilage and recovery from errors made, rather than improving the productivity of the primary fermentation itself. Despite this, in many production methods, such as the process of wine making, there is still a dependence on natural yeast resident on the surface of the grapes and, despite improved cleanliness and modern vessel design, the primary fermentation process used is still very close to that used in ancient times. Similarly, beer, cheese and leavened bread production has not varied substantially from the primary microbial process originally used.

Furthermore, when carbon dioxide is included in drinks there is provided an extra dimension to the taste, texture and thirst-quenching properties of the liquid. The gas is added directly by sparging carbon dioxide into the liquid or, alternatively, can be provided by the action of yeast and dissolved sugars. In certain cases, such as with keg and bottle beers, both methods of carbon dioxide addition may be used. There are a number of liquid drinks that exploit the inclusion of carbon dioxide to provide effervescence to lift and extend the taste and textures of the drinking experience in this way such as non-alcoholic fruit and sugar-based liquids and alcohol based drinks. In all of the above, it is assumed that there is intimate mixing of carbon dioxide with the aqueous medium but it has been discovered, particularly where alcohol is also in the mixture, that the mixing which is conventionally achieved at the molecular level has a negative influence on the overall drinking experience. This is believed to be caused by the natural tendency for water to form erratic intermolecular hydrogen bonds that result in clusters randomly distributed through the medium. Likewise, alcohol is subject to clustering and this leads to a less than optimal distribution of carbon dioxide within the drink product. Thus, certain aspects of the liquid such as for example, the mousse in Champagne which is an in-mouth sensation of carbon dioxide mixed with water and alcohol, are not achieved to the desired extent. A further problem is that adding the gas, by sparging in particular, causes excessive disruption to the open hydrogen bonded structure of the liquid and causes clustering as a consequence. Conventionally, the solution has been to store the liquid usually in containers for long periods to allow the natural kinetic movements to homogenise the system. This can take many years of expensive storage to allow the product to regain the liquid's preferred open structure in which the gas and alcohol can be accommodated homogeneously.

In the more recent past, many of the skills and experience obtained from brewing and winemaking has been exploited in the production of, for example, biopharmaceuticals in which the fermentation systems adopted, and the equipment used, are broadly similar but are required to conform to relatively strict regulatory parameters and the organisms used have been genetically manipulated. However, once again, the growth and performance of the cultures is still fundamentally dependent on the inherent behaviour of the original organism. It is found that these processes can be optimised by a judicious choice of nutrients and careful control of temperature, gas exchange and/or other batch manufacturing conditions, but it is found that microbial productivity cannot exceed the natural limitations of the microbes which are involved.

Furthermore, a common factor in all the above processes, both modern and older, is that there is a requirement for a time period to elapse between the start of the process and the end of the same in order to allow the yeast and/or other organisms to perform their function in the product to the full potential. This time delay can be a significant barrier to the larger scale and more efficient manufacture of the product in a desired form and/or can mean that the end product is of inferior quality if insufficient time is allowed for the complete function to be performed. Thus, commercially significant productivity is restricted or cannot be achieved as it is believed that microbial cultures have now reached their natural limits in terms of productivity and what can be achieved by the optimisation of nutrients, growing conditions, and/or equipment. Thus it is conventionally believed that the processes used in relation to specific products are difficult to alter without compromising the quality and/or violating regulations.

For example, in the field of mammalian cell culture which is used in a number of sectors across the medical and biotechnology industries to generate a wide range of products, including enzymes, hormones and antibodies, the production of biologics using mammalian cells is conventionally very costly due to the slow growth rates of the cells, highly specialised conditions and a higher risk of contamination than the traditional microbial system but it is believed that the conventional approaches are the only viable solutions.

The applicant in their co-pending application PCT/GB2018/053493, the contents of which are incorporated herein, disclose the ability to provide the electromagnetic field in pulses and exposure of the same to certain products to allow a change in the metabolic productivity of biosystems of the liquid, such as fermentation and cell cultures.

However, in order for the application to be effective there is a need to be able to ensure that the electromagnetic field is applied in a reliable and repeatable manner in order to ensure that the effect of the method is achieved on each occasion of exposure of a liquid to the pulsed electromagnetic field.

An aim of the present invention is therefore to provide a solution to the above-mentioned problems which allows the quality and procedures used to obtain the development and desired form of the product, to be improved and thereby improve the quality of the end product and/or speed up the means by which the end product can be achieved. A further aim is therefore to provide a method which is non-invasive, easily applied and can deliver increased yields and/or decrease batch production times.

A further aim of the present invention is to provide apparatus which allows the effective application of the electromagnetic field to the product in a manner which is easily repeatable and which preferably can be performed by a non-skilled person if required. A further aim is to provide the apparatus in a form which allows the same to be used in conjunction with a container in which the product which is to be treated is held.

In a first aspect of the invention there is provided apparatus to allow the application of an electromagnetic field to a product for a period of time to alter the condition of said product, said apparatus including at least one support and a container in which the said product is located and wherein said support includes one or more modules for the generation of a pulsed electromagnetic field (PEMF) and said support includes or is connected to control means to control the generation of the PEMF and is positionable with respect to the said product so as to allow the product to be exposed to said pulsed electromagnetic field which is generated.

Typically the apparatus is provided to allow the transmission of the PEMF to promote intimate mixing of components of the product.

In one embodiment the apparatus control means control the frequency and digital sequence of the PEMF which is emitted to correspond to the dielectric properties and/or other properties of the product which is held in the container at that time.

In one embodiment the control means are provided in the form of an integrated circuit provided on the support and may include a transmitter to allow the emission of a PEMF therefrom in addition to the PEMF's emitted from said modules.

In one embodiment the control means are in turn operable by a software based user interface to allow the user control of the generation of the PEMF from the device.

In one embodiment the support and/or modules are locatable with respect to the container so as to allow the product held in the container to be exposed to the PEMF.

In one embodiment a plurality of said modules are provided in a fixed array or configuration on the support to provide an increased range and/or intensity of PEMF.

In one embodiment the support is located externally of the container and the PEMF is applied to the product through one or more walls of the container in which the product is located.

In an alternative embodiment at least the part of the support which includes the one or modules for generating the PEMF is located inside the container.

Typically a plurality of supports can be located at different locations within the container in order to provide a uniform exposure to the PEMF's generated from modules located with said supports.

In one embodiment the said support is formed by one or more walls of the container and the modules are mounted as part of the said one or more walls. In an alternative embodiment the said support is located within one or more walls of the container.

In one embodiment the support is provided in the form of a housing in which the said one or more modules are located or in another embodiment the support is provided as sheet material on which the modules are located.

In one embodiment the support is provided in a sterilised form for use and in one embodiment may be provided for a single use.

In one embodiment the said modules include an antenna and a transmitter to allow a wireless short-range communication of the PEMF within a specific frequency range. In one embodiment the specific frequency range is the industrial, scientific and medical (ISM) short-range radio frequency band. In one embodiment the frequency is 2.4 GHz.

In one embodiment the transmitter is capable of generating the PEMF up to a distance of 15 metres.

In one embodiment the control means allow the transmission of the PEMF in pulses which are in the range of 0.5-1.5 ms in duration and/or the said pulses are spaced apart by rest periods which are in the range of 40-66 ms and/or the PEMF pulses are emitted within a range of 12-20 pulses per second.

Typically the supports and/or modules located thereon are arranged with respect to the container so as to generate the PEMF in an omnidirectional manner to the product.

In one embodiment the module is based on a personal area network system device.

In one embodiment, the control means and modules which emit the PEMF are provided with the support which is in the form of a radio transparent housing and in which the modules are located and the shape of the housing and spacing of the modules can be adapted to allow the same to be used in relation to one or a range of container types.

In one embodiment the housing and hence apparatus is provided as an integral part of another item which can be used with the container or is formed as part of the container in which the liquid is held.

In one embodiment, the support is provided in a shape, such as a mould that fits a profile of a particular container with which the same is to be used so that the location means of the apparatus allows the secure fitting of the container therewith and hence allow the apparatus, in one embodiment, to be used immediately before the consumption of the product.

In one embodiment the container is any of an individual bottle or glass or may be a group of containers such as a number of bottles or glasses and in which the product is held and which, in one embodiment, is a sparkling liquid and/or contains alcohol such as Champagne, Prosecco, Cava or the like.

In another embodiment the container may be in the form of a bioreactor vessel and it should be appreciated that the container which is used is provided in a form which is suited to the product to be held therein and/or the process steps performed on the product and in relation to which the PEMF is selectively applied as an additional step or during at least one of the steps.

In one embodiment, the apparatus is provided with location means which allow the base of the container to be placed thereon and/or may be provided with engagement means which are placed around the container.

In one embodiment, the apparatus is provided in the form of a housing which fits over the neck of a bottle.

Typically, the apparatus includes a battery or other power supply means and/or can be charged to allow power to be supplied to emit the electromagnetic field pulses.

In another embodiment, the apparatus is provided in a form of a sleeve which may be provided around the container and which may also be provided with means to allow the cooling of the liquid in the container.

In one embodiment, the apparatus includes at least one feature which allows the visual appearance of the container to be changed such as for example, to provide the apparatus with lighting to provide an extra visual dimension when the container is a glass and/or to provide an indication of the operation of the apparatus and as and when the PEMF is being generated.

In a further aspect of the invention there is provided a method for the change in condition of a product, wherein the said method includes a step of applying a pulsed electromagnetic field from one or more modules at a predetermined frequency and for a predetermined period of time to the product when in a first condition to change the said first condition of the product into a desired further product for subsequent use or further processing.

In one embodiment the said change in condition is as a result of the performance of fermentation and/or development of a cell culture system of the product.

In one embodiment the said PEMF allows the change in condition of one or more components of the product in the form of an element or ingredient of the product.

In one embodiment the PEMF is applied as a stage of the treatment of the product so as to cause fermentation and/or cell culture development in the product.

In one embodiment the change in condition is to increase the speed at which a processing step of the product occurs. In one embodiment the processing step is the development of cell cultures.

In one embodiment the PEMF is applied to increase the speed of growth of mammalian cell cultures.

In one embodiment the application of the PEMF is to the product is deliberately not used during other stages of processing of the product.

In one embodiment the PEMF is applied for a predetermined period of time which is determined with reference to a particular product and/or quantity of the product.

In one embodiment the PEMF frequency is within the band width of the electromagnetic spectrum used for industrial scientific and medical purposes.

In one embodiment the electromagnetic energy is delivered in pulses which are in the range of 0.5-1.5 ms in duration.

In one embodiment the pulses are spaced apart by rest periods which are in the range of 40-66 ms.

In one embodiment, a plurality of said devices are provided in a fixed array or are selectively positioned in an array in order to provide a stronger pulsed magnetic field or a pulsed magnetic field with a larger range.

In one embodiment, the PEMF is applied to product held in multiple containers simultaneously using the apparatus with the containers located in a specific array.

In one embodiment the containers are bottles which contain a sparkling liquid such as wine.

In one embodiment, the use of the pulsed electromagnetic field in accordance with the invention provides any, or any combination, of increased productivity in the production of biofuels, cultures of genetically modified cells and organisms, insulin, monoclonal antibodies, growth hormones, interferon, interleukins, blood factor VIIa, blood factor VIII, blood factor IX, erythropoietin, gonadotrophin, glucagon, vaccine antigenic sequences, mammalian cell culture.

Thus, in accordance with the invention, the conventional reactor conditions and equipment can continue to be used for the product formation with the addition of the generation of a pulsed electromagnetic filed to create an environment in which the product is located.

Typically microbial organisms are electrically magnetic systems and respond to changes in electromagnetism.

Typically, the culture is irradiated with the PEMF using the apparatus which includes a radio or microwave transmitter which is positioned so that the use of the apparatus is non-invasive and does not therefore alter any nutrient or recipe component of the product.

In one embodiment, the radiation frequency is preferably 2.4 Ghz.

Typically the pulses are in the range of 0.5-1.5 milliseconds in duration and, more preferably, 1 millisecond duration. Typically, the pulses are spaced apart by rest periods which, in one embodiment, are in the range of 40-60 milliseconds and, more preferably, 50 milliseconds.

The provision of the rest period between pulses ensures that the microorganisms are not overwhelmed by electromagnetic energy but instead are encouraged to increase metabolic processes and increase growth rate. It is found that this results in an increase in expression of metabolites and a more efficient conversion of nutrients into the product hence increasing yields and/or decreasing production time required to achieve the desired result. Furthermore, the rest periods between the pulses allows the activity generated in the product by the PEMF to relax and hence the pulsing promotes homogeneity since clusters are broken apart and a thermodynamically favourable open structure of the product forms naturally.

In one embodiment in order to detect the generation of the PEMF, electronic magnetic field detectors can be utilised in the vicinity of the apparatus. The change in condition of the product may be one or a combination of the features and/or product processes.

In one embodiment the control means allow the frequency and digital sequence of the electromagnetic field which is emitted, to correspond to the dielectric properties and/or other properties of the product which is held in the container at that time.

In one embodiment, the electromagnetic field which is generated is provided in 2.4 GHz pulses and the system provides low field, typically, milliwatts, energy pulses. The circuitry is typically programmed to provide one millisecond pulses of 2.4 GHz at low pulse frequencies between 10 to 20 Hz such that the duty cycle is typically in the range of 1 to 2%.

In one embodiment, the duration of the application of the electromagnetic field pulses is in the range of 30 minutes to 2 hours and which can be performed at the same time as another function if required, such as the chilling of the liquid. It should also be appreciated that the duration of the application of the pulses of electromagnetic field is dependent upon the type and/or quantity of the liquid which is being treated.

The range of frequency at which the PEMF is generated is known as an industrial scientific and medical band and the characteristics are generally that the same is provided as a low field or low energy in the milliwatt range, and is provided with short pulse widths of approximately 1 millisecond and has a low frequency pulse rate of typically 15 Hz.

Generally, this form of electromagnetic field is used for services in, for example, a smartphone using a Bluetooth and the same can be modified to delivery these frequencies.

The invention therefore allows a significant improvement in terms of a reduction in the time taken for the component to enter into the exponential phase, thereby allowing a reduction in the overall cycle time of processing of the fermented component. For example, in the manufacture of bioethanol, the improvements which are detailed herein, allow a significant reduction in the production time and thereby allow improved throughput and yield from the same apparatus as would conventionally be used.

In one embodiment, the use of the PEMF is controlled so as to be used in aerobic conditions and in one embodiment, there is provided the application of PEMF to a material in an aerobic environment. In another embodiment, the method is used in the production of butanol from *E. coli* to form a biofuel.

Thus, in accordance with the invention, the use of the method and the apparatus described herein to provide the pulsed electromagnetic field allows enhanced and improved production without adversely affecting the quality of the product.

BRIEF DESCRIPTION OF THE DRAWINGS

Specific embodiments of the invention are now described with reference to the accompanying drawings.

FIGS. 30-35 relate to mammalian cell culture test results in accordance with one embodiment of the invention.

DETAILED DESCRIPTION

Figure 26:
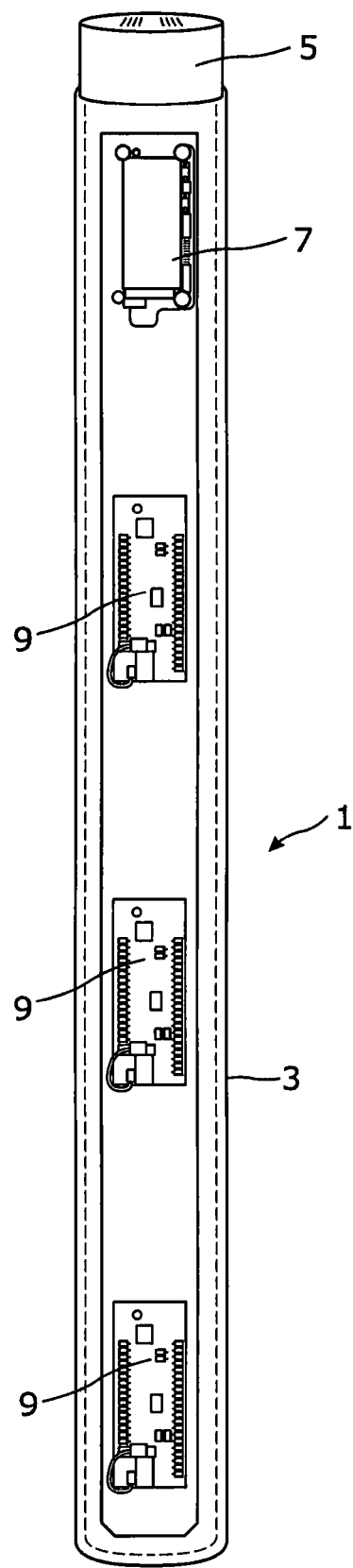
FIG. 26 illustrates an embodiment of apparatus for use in introducing the pulsed electromagnetic field into a container in which the product to be treated is located.

Referring firstly to FIG. 26 there is illustrated an embodiment of apparatus which can be used to introduce the pulsed electromagnetic field into a container in which the product to be treated is located.

In one embodiment the probe 1 is provided with an outer housing 3, such as a glass tube which in one embodiment has a sealing cap 5 which secures to the glass housing 3 at one end and has a suitable attachment configuration, typically including a flange to allow an airtight seal to be created, which allows the same to be attached to the walls or another component of the container into which the probe 1 is to be inserted to thereby mount the probe in affixed position. The majority of the probe, typically the glass housing 3 will be located within the container. Within the housing 3 there is provided a printed circuit board 7 with parallel circuit traces for modular power and series circuit traces for module data feedback and programming input. The circuit board also includes a battery which can be recharged and it will therefore be appreciated that the printed circuit board acts as a means to provide power to the modules 9 and to provide control data to and from the modules so as to operate the same in the required manner.

The series of spaced modules 9 which are located in a required configuration for the particular use and which in this case are equi-spaced along the length of the housing 3. Each of the modules is capable of emitting the pulsed frequency through the housing walls and into the container so as to impact on the product held within the container. The provision of the modules 9 located on the core support 11 allows the suitable spacing of the modules 9 from the walls of the housing 3 and therefore provides a degree of heat insulation from heat which may be created due to other processes within the container such as sterilisation processes and which therefore enable the housing to be sterilised by steam and in one embodiment the core 11 can be removed during this process and then reinserted into the housing.

Figure 27:
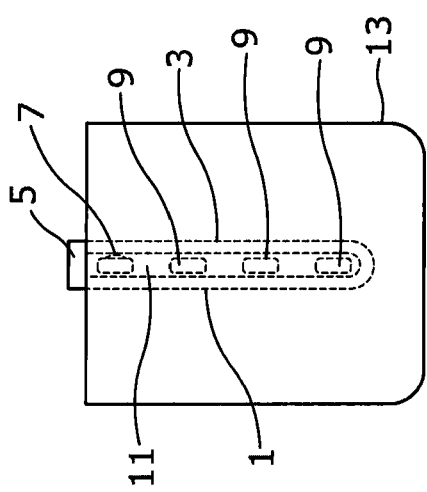
FIGS. 27 and 28 illustrate potential uses of the apparatus of FIG. 26 with a container.
Figure 28:
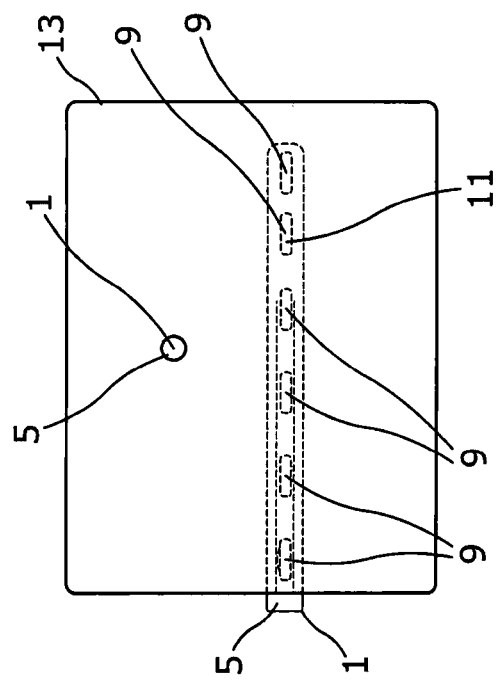

FIGS. 27 and 28 illustrate potential different uses of the probe 1 in accordance with the invention, and in FIG. 27 there is shown the probe 1 having bee introduced into the interior of a container 13 from the top of the same so that the probe is centrally and axially positioned in the container to allow the electromagnetic field pulses to be emitted therefrom through 360 degrees around the probe and thereby provide substantially uniform treatment of the product within the container.

FIG. 28 illustrates the manner in which a plurality of probes 1 can be provided with the same being located through respective ports in the container wall and in this embodiment the probes 1 extend into the container 13 horizontally and are offset by 90 degrees so that there is provided electromagnetic field pulses from each of the probes. It is envisaged that this and other multi probe configurations may be suitable for use in larger capacity containers and/or with products held within the container which benefits from more intense exposure to the electromagnetic field.

Figure 29:
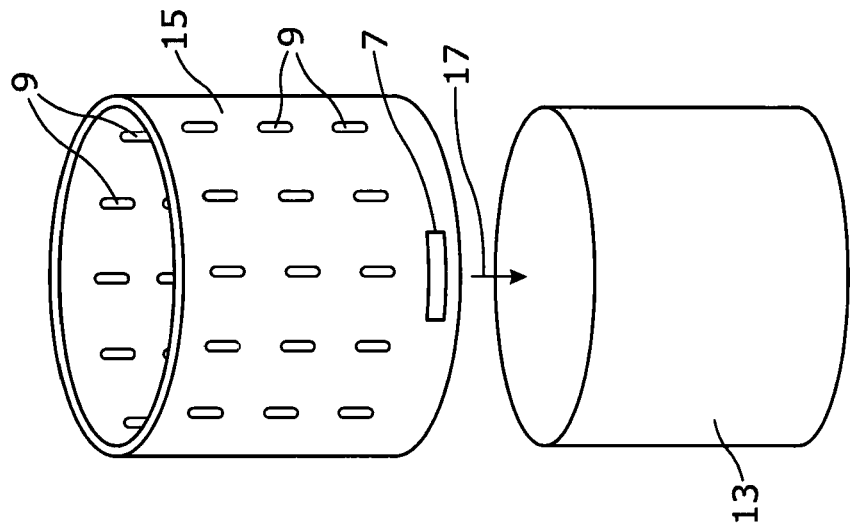
FIG. 29 illustrates a further embodiment of apparatus in accordance with the invention.

FIG. 29 illustrates a further embodiment of the apparatus in which there is again provided a container 13 which includes the product which is to be treated therein. In this embodiment a sleeve 15 is provided which is cylindrical in shape and which has located in a selected matrix configuration a plurality of modules 9 for the emission of the pulsed electromagnetic filed therefrom and also a control module 7 which is connected to each of the modules, typically by wires located integrally with the cylinder material to allow power and control data to be transmitted and received from the modules 9. In the embodiment shown the sleeve 15 can be moved as indicated by arrow 17 to be positioned around the container or in another embodiment, and particularly for use with containers which are repeatedly used for the same purpose, the sleeve may be provided as an integral part of the walls structure of the container or the modules may be provided in the required matrix configuration and be located with the wall structure without the need for the supporting sleeve.

Figure 1:
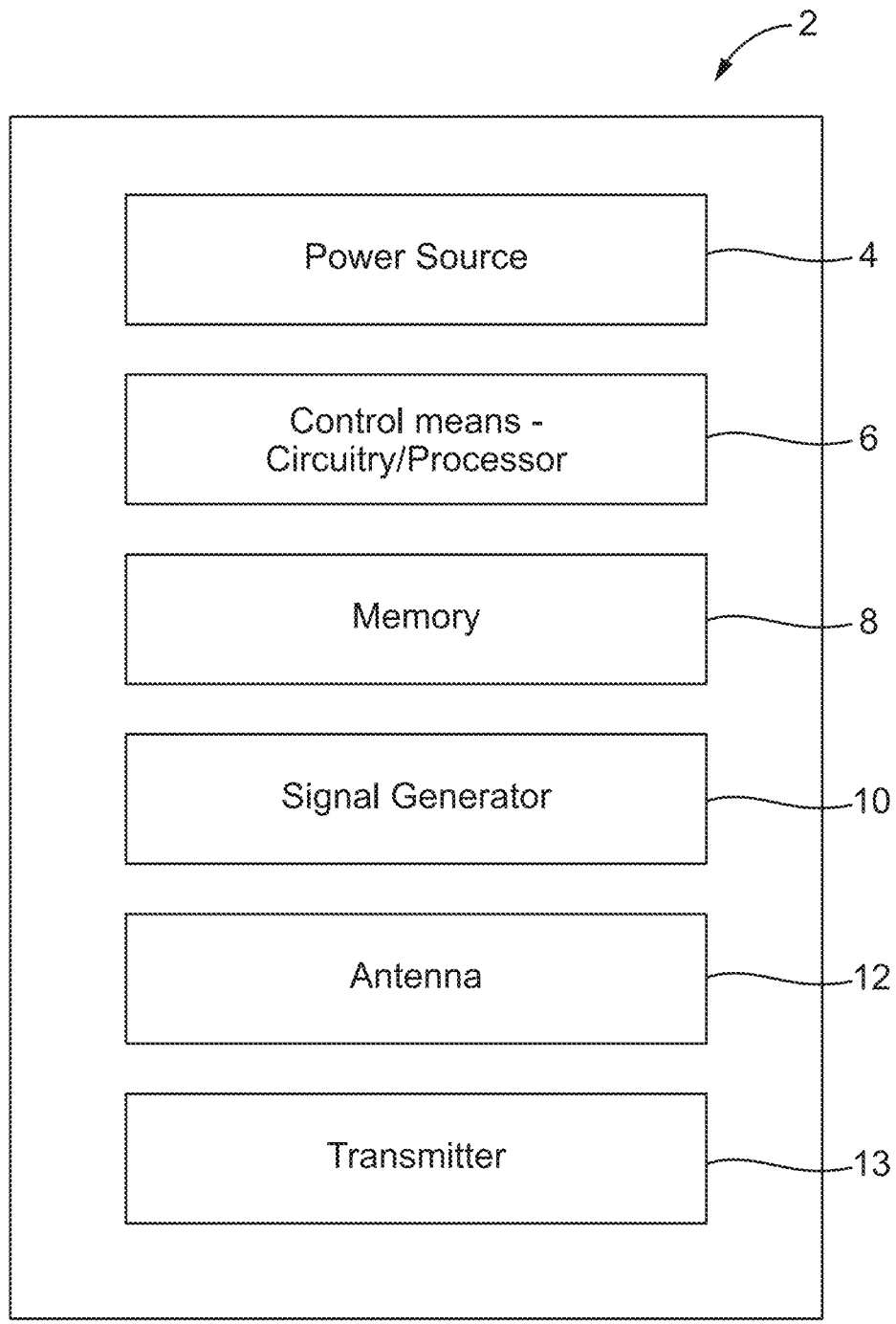
FIG. 1 illustrates schematically apparatus used in accordance with one embodiment of the invention.

Referring now to FIG. 1 there is provided a further form of apparatus in accordance with the invention and in this embodiment the apparatus is provided in this embodiment to treat live cultures of microbial systems, typically provided as part of a product and to enhance their productivity. This is achieved by exposure of the culture to pulsed electromagnetic fields (PEMF) of relatively low energy, typically in the order of microwatts per litre of culture medium, at a frequency which can be in the microwave region and pulsed at low frequencies, for example 10 to 200 Hz. It has been found that this method step improves the growth rate and expression levels of the microbial culture.

In one embodiment the transmission of the PEMF can be from one or more modules which include the control means, and a transmitter 13 similar to that used in a Personal Area Network system and which can be controlled to allow the PEMF to be generated from the module and which is powered by a battery or directly from an electrical source. FIG. 1 illustrates an example of the components which are required to generate the PEMF from a module 2 including a power source 4, a data processor 6, a memory 8, a signal generator 10 and an antenna 12.

The module 2 may be placed underneath or against a microbial culture 16, for example a fermentation of yeast within a sugar-based medium to produce alcohol and carbon dioxide. The fermenter can be exposed from either direction since the signal generated is omnidirectional and not dependent on position but merely proximity, preferably touching the wall of the fermentation vessel.

Figure 2:
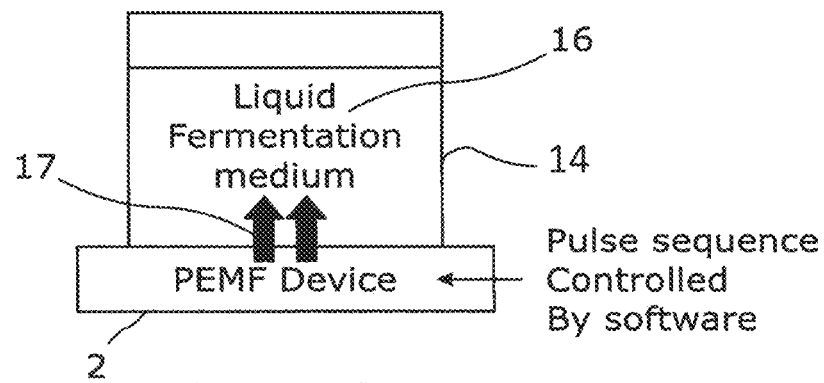
FIG. 2 illustrates the manner in which a device for emitting the pulsed electromagnetic field is used in conjunction with the product medium which is to be treated.
Figure 3:
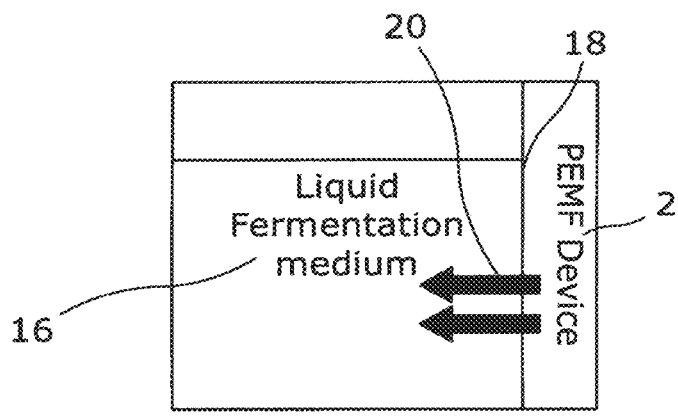
FIG. 3 illustrates an alternative arrangement of the device in relation to the product medium.

FIG. 2 shows one possible arrangement where the module 2 is positioned beneath the vessel 14 in which the culture medium 16 is located so that the electromagnetic field pulses move upwardly as indicated by arrows 17 through the culture. However, as the module is omnidirectional in terms of the direction of emission of the pulsed electromagnetic field then other formats are possible, such as that shown in FIG. 3 in which the module 2 is mounted to a side 18 of the vessel 14 so that the PEMF can be applied in the direction indicated by arrows 20.

Figure 4:
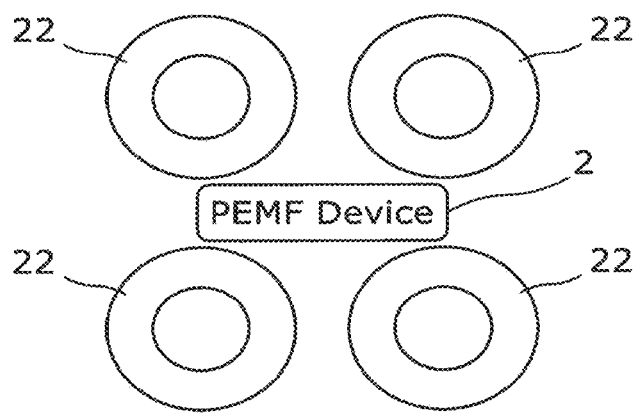
FIG. 4 illustrates the use of the device in conjunction with containers in which the product medium to be treated is contained.
Figure 5:
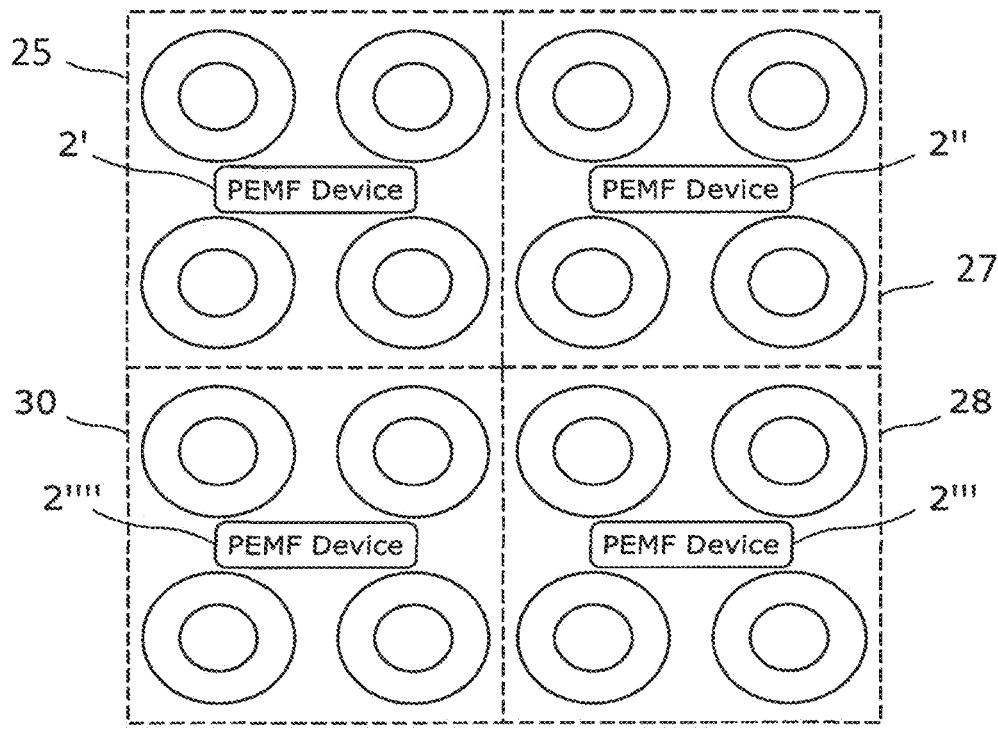
FIG. 5 illustrates a further embodiment of the arrangement of FIG. 4.

In a further embodiment multiple fermentation or bioreactor vessels may be treated simultaneously as shown in FIGS. 4 and 5. For example in FIG. 4 several containers 22 which in this example include a product in the form of a fermented alcoholic beverage are shown in a view from the top. The beverage may be sparkling wine or unpasteurised bottled beer and the containers such as bottles 22 are located around the module 2 as shown such that each bottle 22 is equidistant from the PEMF antennae 12 of the module 2 and therefore the fermentation components in the product 16 in each of the bottles receives the same exposure to the PEMF.

In FIG. 5 there is shown another embodiment of multiple containers 22 of fermenting microbial cultures which are be exposed to PEMF from an array of modules 2. In this embodiment multiple containers 22 are exposed to the PEMF simultaneously with the array formed such that a module 2' services a group 25 of four containers, a second module 2" services the group 27 of containers, module 2" services the group 28 of containers and module 2" services the group 30 of containers. It will be appreciated that the array can be organised such that it is easily transported and fitted during storage such that these containers and the culture contained within can be exposed for a set period of time before moving to a new group of containers for exposure.

Figure 6:
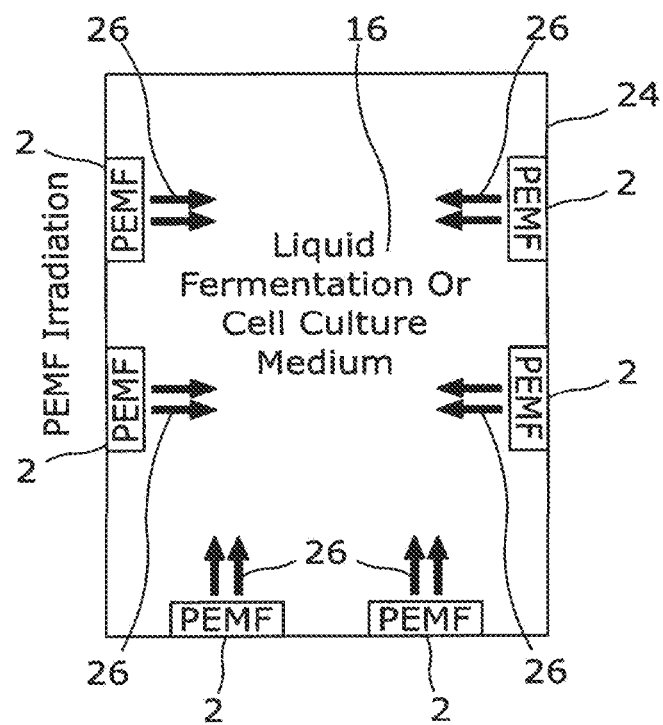
FIG. 6 illustrates the manner in which the one or more devices can be used as part of a circulating apparatus.

For larger scale generation of PEMF for fermentations or cell cultures the modules 2 may be contained in a waterproof, sterile support in the form of a housing that is transparent to the electromagnetic frequency being employed. The PEMF modules 2 so described can be placed around the vessel wall 24 so as to provide an extensive array of said modules which emits the PEMF as indicated by arrows 26 into the medium 16 within the container vessel as shown in FIG. 6. In another embodiment the modules may be placed within a support in the form of a circulating sidearm such that the product flows by the modules and receives PEMF irradiation as it does so. These embodiments are particularly suited to large scale microbial cultures. It is postulated that the treatment with PEMF of the general descriptions described here provides electromagnetic disturbance to charged surfaces within the living cells that provoke increased growth and/or expression of metabolites.

In the case of bottles of sparkling wine, it can be reasoned that the increase in Carbon Dioxide production improves the mousse and texture of the effervescent wine in the mouth. In other product types including alcohol the alcohol activation can create productivity gains as yeast in this case are provoked and encouraged by PEMF to produce more alcohol (ethanol principally). In this case the alcohol may be that contained within fermented drink products such as wine and beer or fermented mash prior to distillation.

Increased productivity by the methods described herein to provide additional and/or higher rate of production of alcohol in the manufacture of biofuels is also described as a use of this invention.

Figure 7:
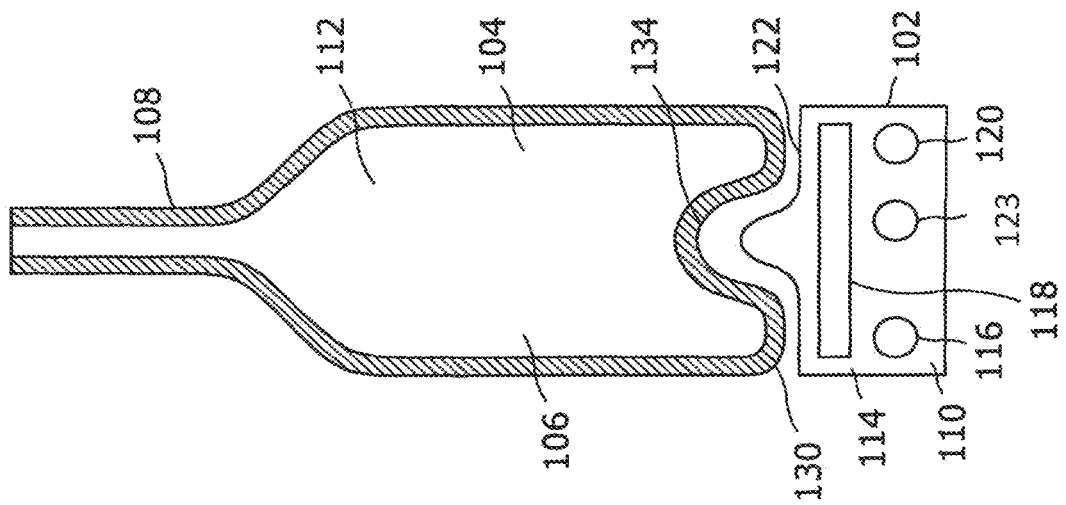
FIG. 7 illustrates apparatus in accordance with one embodiment of the invention and indicating the control means components for use therewith.

In FIG. 7, there is illustrated the apparatus 102 with a housing 110 with the components which allow the apparatus to be useable to generate an electromagnetic field in pulses into liquid 112 which is held within the bottle. The apparatus components include a power source, in this case a battery 114 which is located within the housing 110. The battery may be rechargeable or may be changeable when expired.

A switch 116 is provided to allow the apparatus to be turned on and off and a visual display 118 can be provided either in a format to simply indicate the operation of the apparatus and/or supply of power to the apparatus 102 or in other forms in which the same provides a decorative effect in addition to the functional effect such as, for example, being provide to display a logo of a company who may, for example, be a producer of the liquid in the bottle with which the apparatus is to be used.

Another indication is provided in the form a light source 120 which can illuminate once a sufficient period of time of emission of the electromagnetic field has passed for the quantity of liquid to have been treated effectively so as to indicate that the use of the apparatus can be stopped and the liquid 112 will have been conditioned using the electromagnetic field for a sufficient period of time.

Timing means 123 can be provided which allows the user to select a particular time of operation of the apparatus in conjunction with the bottle and liquid held therein. It should be appreciated that in addition to the above components, there will also be provided within the housing 110 electrical control circuitry and components for the control of the emission and generation of the electromagnetic field in pulses in the required format and the housing wall 122 is provided to be effectively transparent to the electromagnetic field so as to allow the same to pass therethrough and into the container 104 when the same is located therewith.

Figure 8:
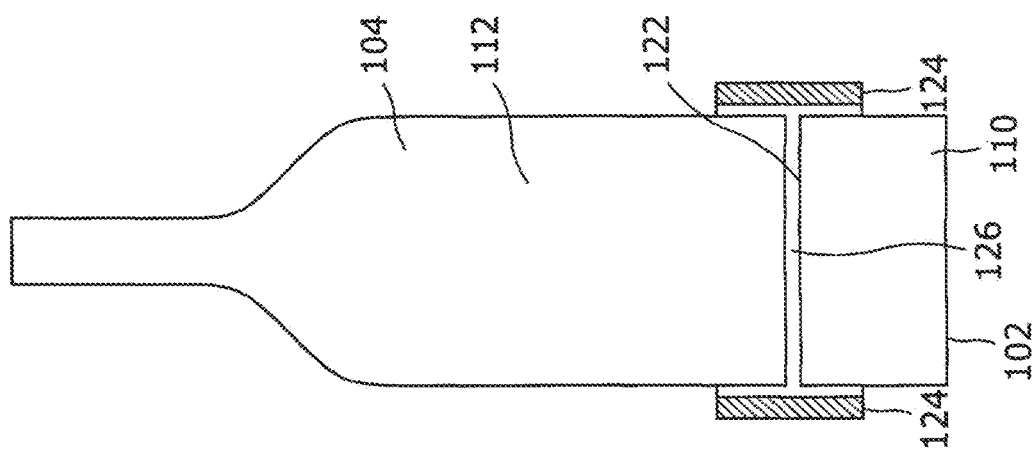
FIG. 8 illustrates the apparatus in accordance with one embodiment of the invention and fitted to a bottle.

FIG. 8, illustrates an embodiment of a means by which the housing 110 can be located with the bottle 104, in this case, by the provision of a sleeve 124 shown in cross section, which passes around the bottle 104 and the apparatus housing 110 at the interface 126 between the same and engages the same together.

Figure 9:
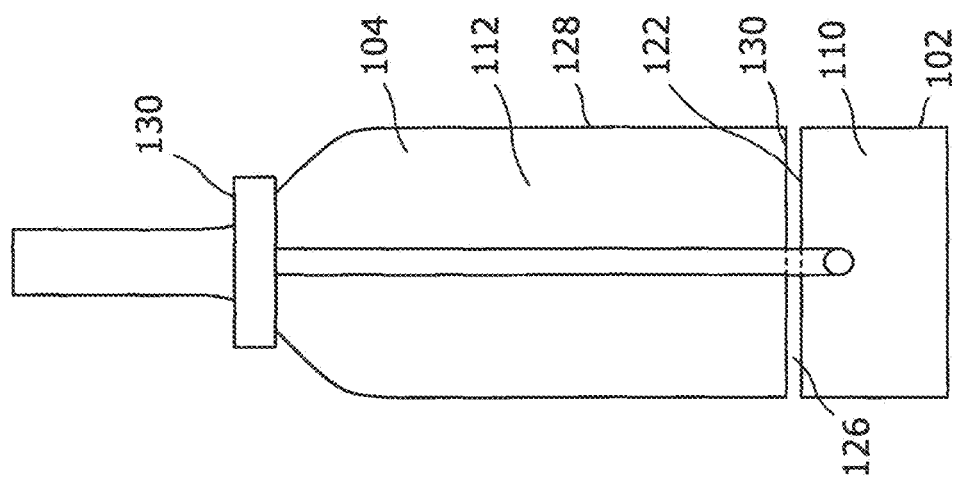
FIG. 9 illustrates an alternative form by which the apparatus can be located with a bottle.

In FIG. 9, there is illustrated the provision of another embodiment of engagement means in the form of a strap 128 which locates with a collar 130 and the collar passes around the neck 108 of the bottle and the strap 128 extends from the apparatus housing to the collar and thereby retains the apparatus housing 110 in contact with or adjacent to the base 130 of the bottle at the interface 126. Typically, the strap will be provided to be elastic and hence bias the apparatus 102 towards the bottle base 130.

Figure 10:
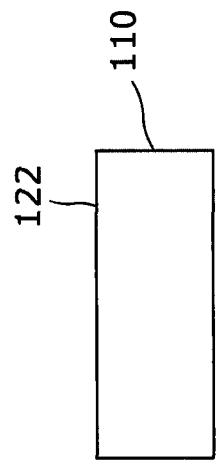
FIGS. 10 and 11 illustrate alternative embodiments of the apparatus to allow engagement with a bottle.

In FIG. 10, there is illustrated the manner in which the apparatus housing can be shaped so as, in this embodiment form the surface 122 with a protrusion 132 which is shaped so as to be located in an indentation 134 in the base 130 of the bottle as illustrated in FIG. 7.

Figure 11:
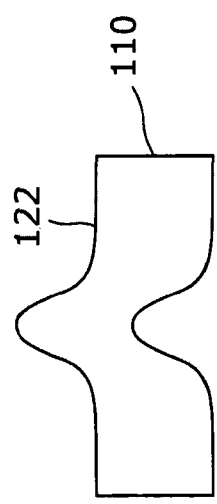

Alternatively, as shown in FIG. 11, the location means of the apparatus can simply be a flat portion 122 on the housing 110 and onto which the container 104 is placed and is freestanding.

Figure 12:
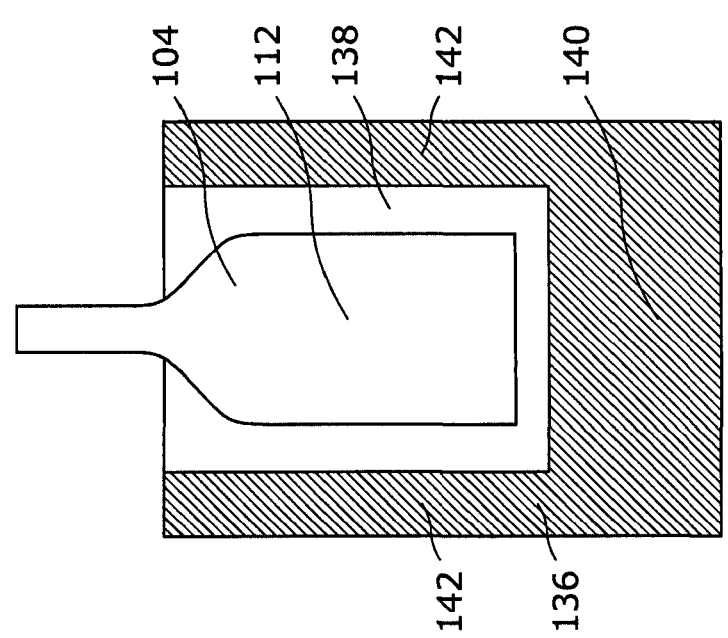
FIG. 12 illustrates an alternative embodiment of the apparatus.

In other embodiments, the apparatus can be incorporated into items which have other functions and in FIG. 12, there is shown a cooling sleeve 136 which is provided with cooling means therein to allow the bottle 104, when placed in the cavity 138, to be cooled. In accordance with the invention, then in addition to the cooling means, there are also provided the components as described with regard to FIG. 1 which are provided in the base 140 and/or side walls 142 to emit the electromagnetic field from the sleeve and into the liquid 112 held in the bottle 104.

Figure 13:
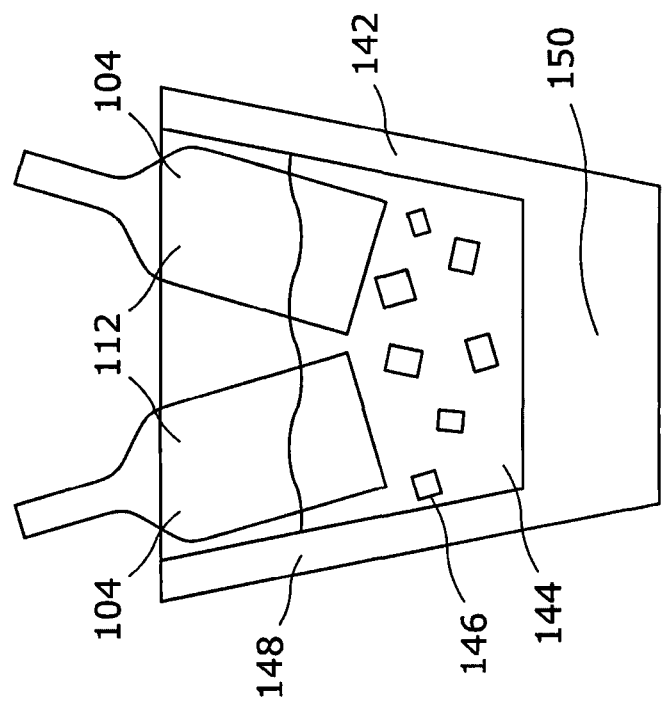
FIG. 13 illustrates the incorporation of the apparatus with another item.

In FIG. 13, there is illustrated an ice bucket 142 which has a cavity 144 for the reception of ice and water 146 therein and, in addition, the base 150 and/or walls 148 of the ice bucket are provided with the appropriate circuitry to allow the electromagnetic field to be generated from the same and into the liquid in the bottles 104 when held in the cavity.

Figure 14A:
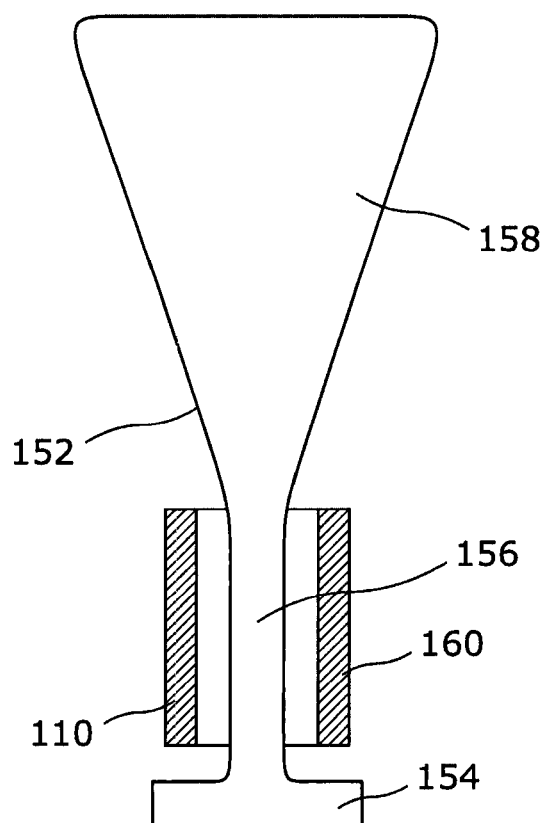
FIGS. 14a-d illustrate further embodiments of apparatus in accordance with the invention which can be used in conjunction with a container in the form of a glass.
Figure 14B:
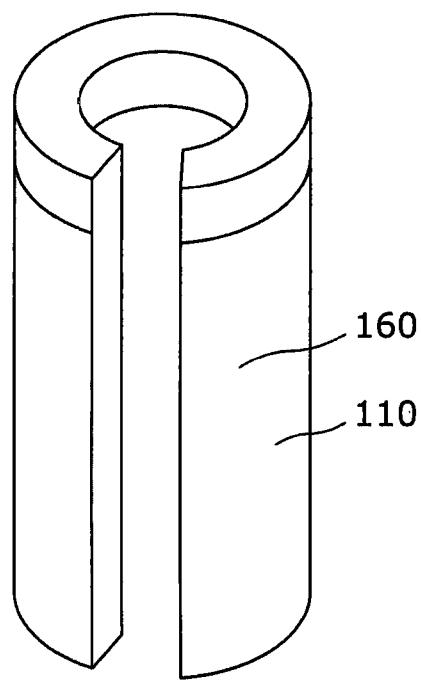
Figure 14C:
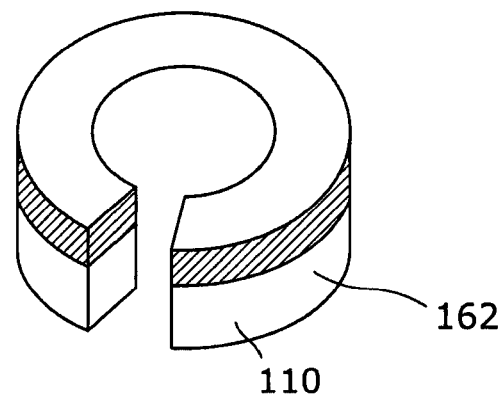
Figure 14D:
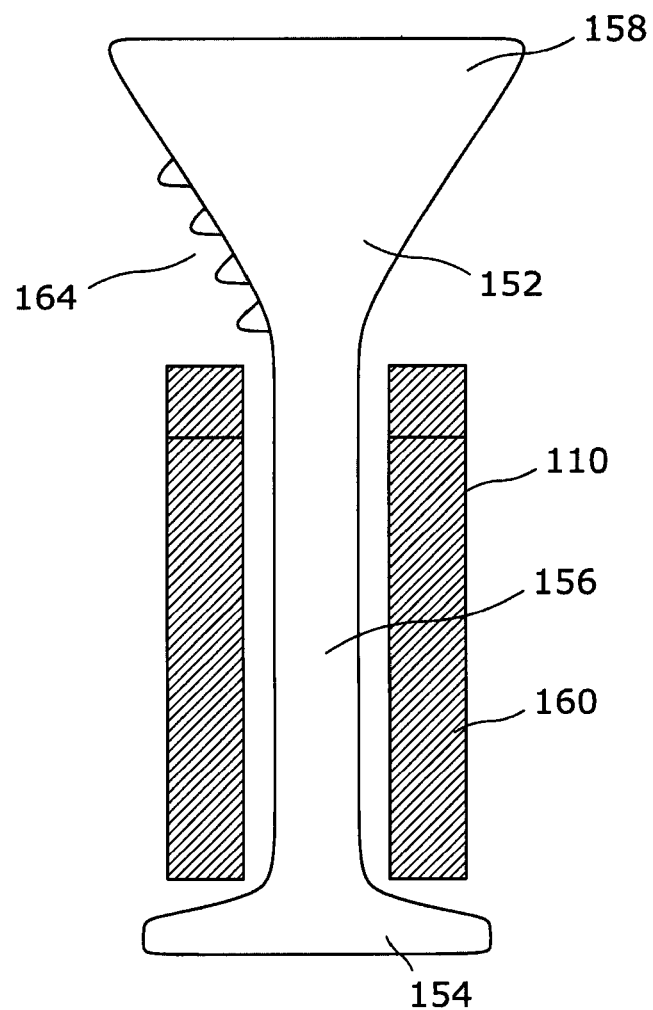

Turning now to FIGS. 14a-d, there is illustrated a container in the form of a glass 152 which has a base 154, a neck portion 156 and a cavity portion 158 in which the liquid is held. Once again, the apparatus housing 110 can be provided in a number of different forms which, as shown in this case, includes a sleeve 160, or a collar 162. Typically, the same components will be included in the apparatus regardless of the particular type of container with which the same is to be used and in one embodiment, the lighting means 164 provide both a functional effect and also as a visual decorative effect on the part of the glass as illustrated in FIG. 14d.

Specific examples of use of the apparatus and method as herein described with respect to FIGS. 1-14d, are now provided;

Example 1—Growth Rate in Yeast within a Typical Home Wine Fermentation

Experiment conducted in Haddenham Buckinghamshire from 7 May 2018 to 14 May 2018

Two commercial wine kits were obtained and prepared and initiated identically in 5 litre demijohns. The yeast provided was added and the two cultures separated by more than 30 feet. A smartphone was placed to lean against the glass of one of the demijohns (the active sample). The smartphone, a Galaxy S4 had been loaded with an app that took control of the personal area network, PAN, microwave system (tradename Bluetooth) that delivered pulsed electromagnetic fields with the characteristics detailed below. The other demijohn was left to follow un an irradiated normal fermentation (the control sample)

Irradiation Procedure

The smartphone with specialist app in active mode, was placed against the outside of the active demijohn. The control app is used to control the PAN and provides 2.4 GHz in 1 millisecond pulses at a pulse rate of 15 Hz. The smartphone was left in active mode for 2 hours. This was repeated every 12 hours (that is 2 hours of active pulsed irradiation) for one week.

The demijohns were observed regularly, and it could be seen that carbon dioxide production in the active demijohn, as evidenced by bubble rate via the air lock system, was on average at day 3, more than double that of the control.

Bubble Production Rate on Day 3

Active demijohn: 9 bubbles per minute

Control Demijohn: 4 bubbles per minute

At the end of one week the lees (spent yeast cells) was observed and compared to the control demijohn. It could be seen that significant extra growth had occurred in the active sample as evidenced by the depth of lees.

Active sample: Depth of lees 180 mm
Control Sample: Depth of lees 80 mm

Increase of 225% yeast growth indicating increased metabolism and hence increased productivity of alcohol and carbon dioxide (as evidenced above by bubble production rate)

Example 2 Live, Bottled-Conditioned Beer

Experiment Conducted over 2 days from 10 May 2018 to 12 May 2018 at Haddenham Buckinghamshire Sample was 500 mls St Austell Brewery, "Proper Job" India Pale Ale (a live bottle conditioned beer, which has not been pasteurised and therefore has live yeast remaining in the bottle that can respond to Pulsed Electromagnetic Fields.

Two bottles of the above beer were purchased from the same shelf of Waitrose in Thame Oxfordshire and then separated at the premises in Haddenham by at least 30 feet to ensure only the active sample received PEMF from a smartphone.

A Galaxy S4 smartphone, which was loaded with the appropriate app, purchased from the Google Play store, was placed against the bottle of live beer with the app activated an in active mode. This was the active sample.

The active sample was treated as above for two hours, twice a day for 2 days.

The other bottle of identical beer, which was at least 30 feet distant from the smartphone was left untreated, that is in the absence of PEMF. This was the control sample.

After 2 days the bottles were opened and poured into large beer glasses and observed for characteristics. The two beers were then tasted and assessed for sensory differences.

Active beer: this was seen to be significantly more effervescent with pouring having to be interrupted to allow foam to settle. When in the glass the gas foam on top of the beer lasted for 8 minutes and bubbles were seen rising continually for 20 minutes. By comparison to the control the colour of the beer was 2 shades deeper in amber hue.

On tasting it was evident that the beer had a creamy silky texture and was extremely flavoursome by comparison to the control. The beer also had length and finish which was noticeably different to the control, see below Control Beer: the beer could be poured without interruption with the foam being consistently retained within the glass. The foam head quickly disappeared, within 2.5 minutes and bubbles ceased within 4 minutes.

On tasting, the control beer lacked the creamy and velvety texture of the active sample and there was less influence of effervescence delivering flavour in the mouth. The finish was short and lacked definition of flavour by comparison to the active sample.

Example 3: Sparkling Wine (Cava and Champagne)

Experiment Performed at Haddenham Buckinghamshire between 14 May 2018 and 21 May 2018.

3 pairs of sparkling wine were selected from Waitrose in Thame Oxfordshire. 1 pair of Bollinger Champagne, one pair of GH Mumm Cordon Rouge Champagne and one pair of Waitrose own-label cava.

The pairs were separated with one each to become the active samples the other part of each identical pair were separated by at least 30 feet.

The active 3 bottles were placed together with a Galaxy S4 smartphone in the middle of the trio such that each bottle was equidistant from the smartphone. The smartphone was loaded prior to the experiment with the appropriate application. This app when activated takes control of the PAN system and delivers 1 millisecond pulses of 2.4 GHz at a pulse rate of 15 Hz.

The smartphone with the app activated was placed as described above between the active samples for 2 hours, twice per day for the duration of the experiment. After 7 days treatment the bottles were combined with their control pairs and chilled before tasting.

The tasting of the sparkling wine was performed by the head tasters (Head Noses) at Corney and Barrow wine importers at their tasting laboratory on their premises at 1 Thomas Moore Street, London.

Results of tasting: Each of the sparkling wines was opened as normal but it was noted that the treated sample in each case had a louder and lower frequency "boomy" pop on opening.

The treated samples produced more bubbles in the glass by comparison to the control and the bubbles lasted considerably longer in the glass. The "noses" each commented on the dramatic improvement to the "mouse" which was described as being like smooth silk.

Each of the "noses" commented that in each case, Bollinger, Mumm and Waitrose Cava, the overall quality of the drinking experience was enhanced.

In other embodiments the above arrays of modules 9, 2, both external and internally of the container in which the product is held can be selectively to provoke increased productivity in industrial products fermentations such as aspergillus producing for example citric acid for the drinks industry In another embodiment the product cell culture or fermentation receiving PEMF is a genetically modified organism. In this case the required metabolic product may be Insulin from modified yeast or other biopharmaceutical proteins such as monoclonal antibodies, other hormones such as glucagon, growth hormone, gonadotrophins, Haematopoietic factors such as erythropoietin or colony stimulating factors. Proteins that would also improve in yield or productivity include without limitation, interferons, interleukins and blood factors such as Factor VIIa, Factor VIII and Factor IX. Also, thrombolytic agents manufactured by cell culture include tissue plasminogen factor. In addition other biopharmaceutical products that can receive increased productivity according to the invention are vaccines such as hepatitis B or influenza antigens.

The electromagnetic modulation may have different frequencies and wave form shape. There may also be many pulse frequencies that suffice to encourage growth in fermenting and cultured microbial systems.

In practice the use of electromagnetic frequencies is governed by legislation. The band surrounding 2.4 GHz is chosen as it is believed that this provides a good balance of modulating electric field and the dielectric properties of water such that water rotates in the presence of 2.4 GHz. Also 2.4 GHz and its neighbouring frequencies are license free and set aside by international governments for use by Industrial, Scientific and Medical communities. The so-called ISM band.

In different embodiments, the duration of pulse, the pulse frequency and electromagnetic frequencies may be varied according to the product culture to be treated and the duration of treatment may be varied from a few hours to several days or weeks and the exposure to PEMF may be continuous or given periodically.

Turning now to FIGS. 15-18c there is illustrated graphically results of a comparison between a control quantity of *E. coli* and *E. coli* which has been treated using PEMF in accordance with an embodiment of the invention.

Figure 15:
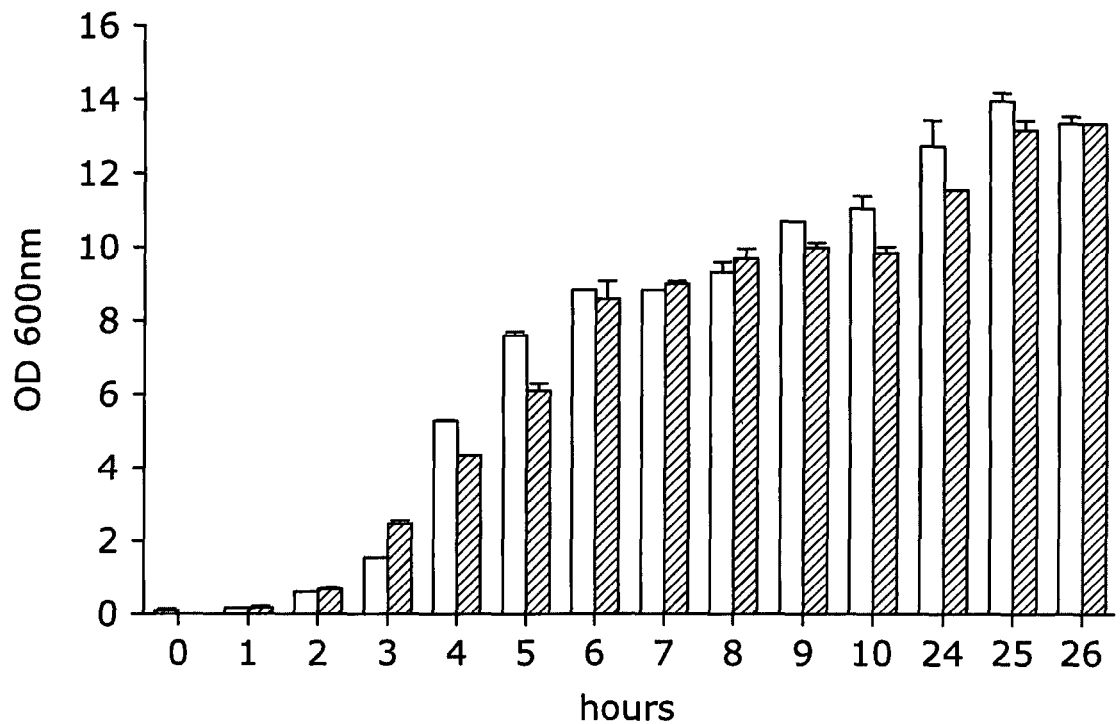
FIG. 15 illustrates, graphically, comparison between a control quantity of *E. coli* and *E. coli* which has been treated using PEMF with regard to optical density in relation to time.
Figure 16:
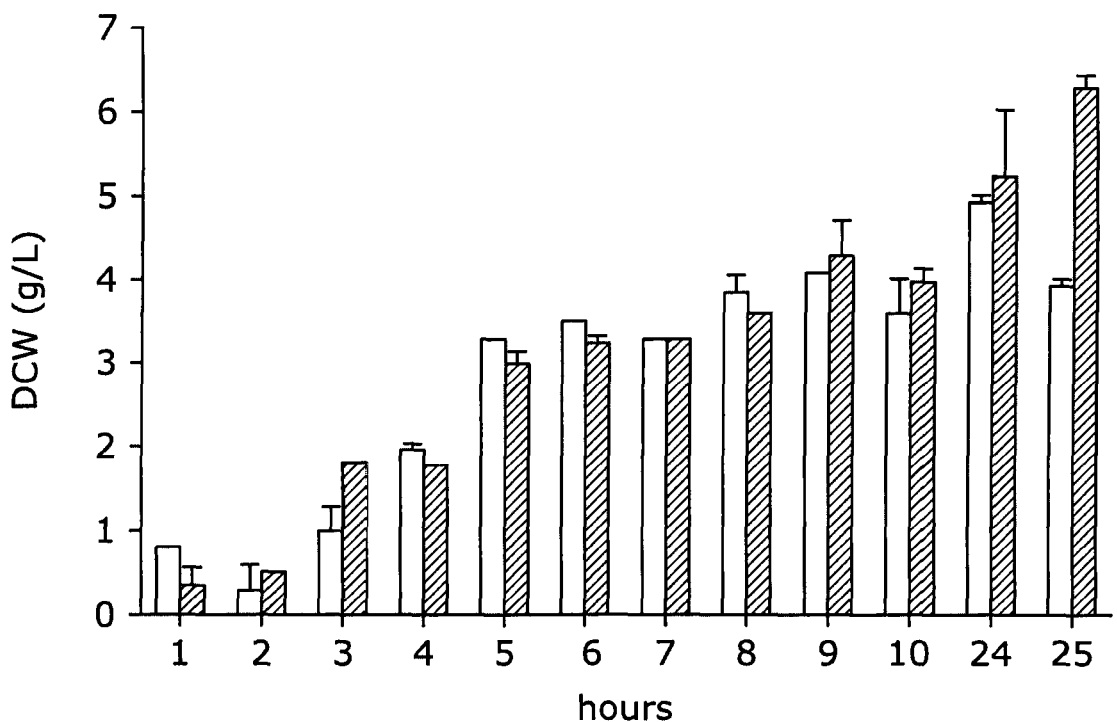
FIG. 16 illustrates a comparison between the control quantity of *E. coli* and the *E. coli* treated using PEMF with regard to dry cell weight over time.

Referring firstly to FIG. 15, the graphical illustration shows that while measurements of the optical density at 600 nm do not show any significant difference between the controlled fermentation and the material which has been treated using PEMF, FIG. 16 shows that the final cell concentration in terms of the dry cell weight in grammes per litre g/L reached after 24 hours of incubation, had increased by 57% for the material which has been exposed to PEMF rather than the control quantity of *E. coli*.

Figure 17:
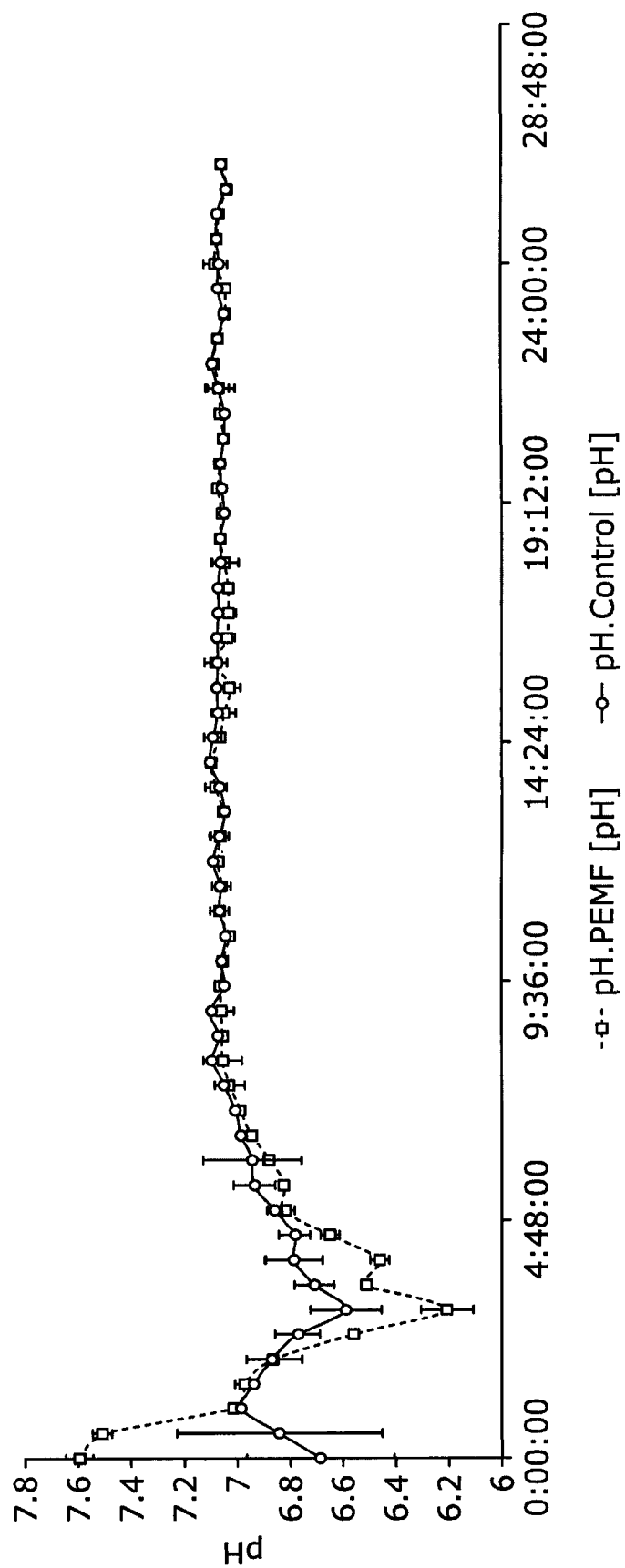
FIG. 17 illustrates graphically, a quantity of *E. coli* as a control and a quantity of the *E. coli* which has been treated using PEMF in accordance with the invention in relation to pH value over time.

FIG. 17 illustrates that with regard to pH, then despite the control *E. coli* having a different starting pH of 6.68 compared to the pH value of 7.59 for the *E. coli* treated using PEMF, the pH was controlled in both experiments at a value of 7 and, in the PEMF fermentation, the acidifying activity of the cultures was far stronger than in the *E. coli* which was not exposed to PEMF. Although the control system could not adjust the pH value fast enough to cause the decrease of pH down to 6.20 against 6.58 for the control portion of the *E. coli*, this could mean that PEMF has been responsible for higher organic acid production.

Figure 18A:
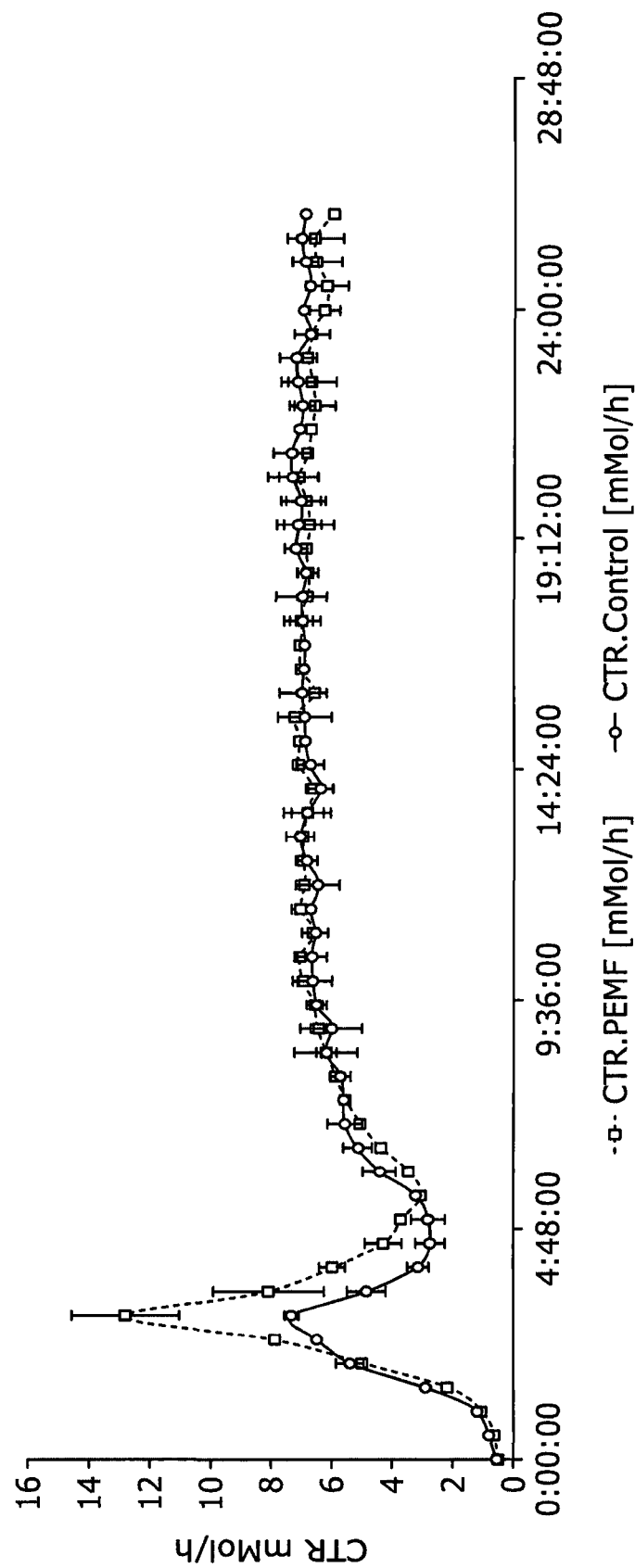
FIG. 18a illustrates the control and PEMF treated quantities of *E. coli* with regard to cell respiration over time.

With regard to FIG. 18a then there is an overall higher metabolic activity with respect to the quantity of the material which has been exposed to PEMF as the $CO_2$ produced and released into a medium, is significantly higher at 74% than in the control portion of *E. coli*. Thus, this means that the cell respiration is more important under PEMF conditions and, by consequence, the production of secondary metabolites such as formate and acetate occurs and which may explain the sharper decrease of the pH value which is observed.

Figure 18B:
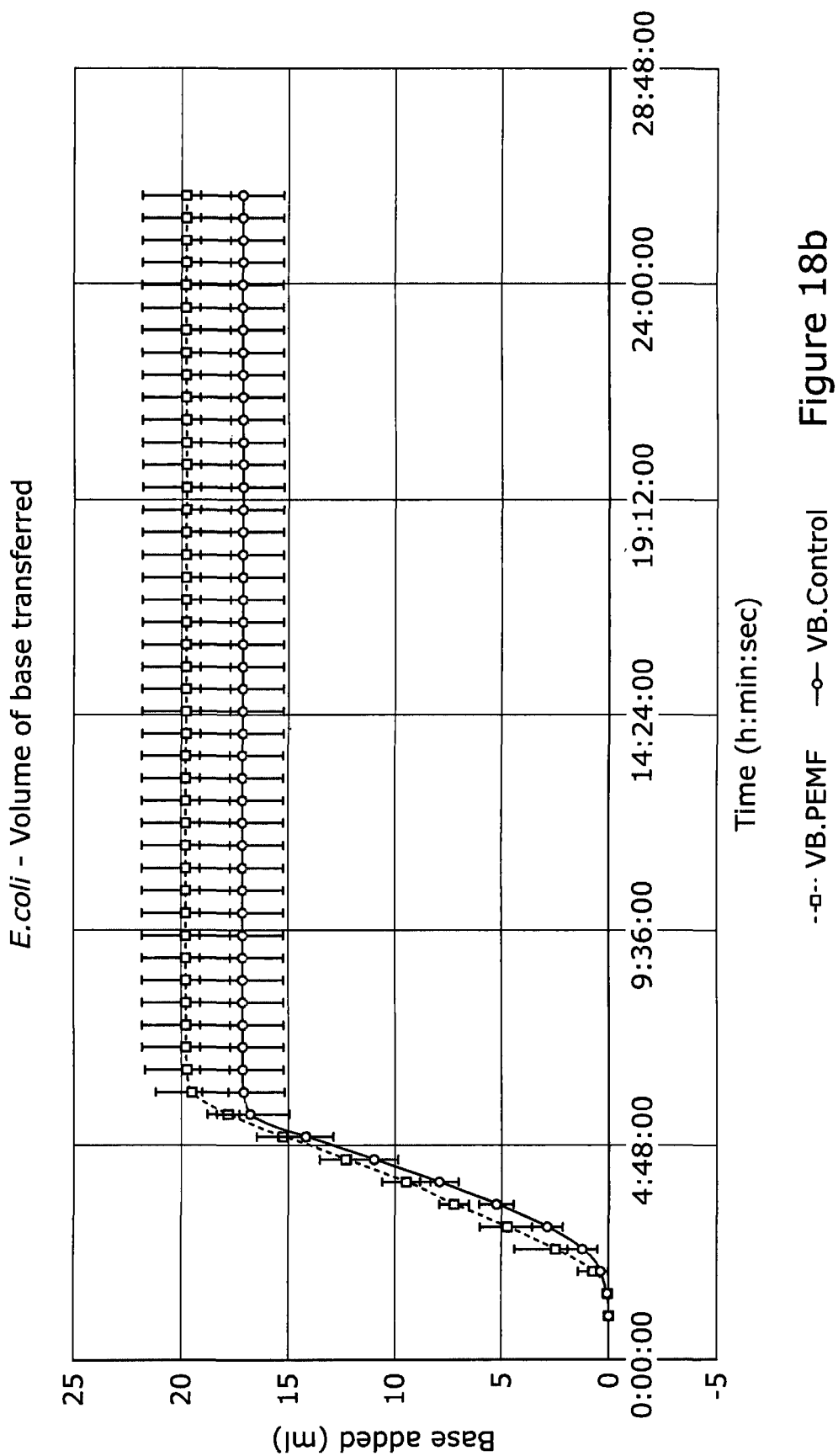
FIG. 18b illustrates acid production in *E. coli*.

FIG. 18b illustrates that for the material which is exposed to the PEMF the total amount of base transferred into the fermenter to raise the pH was greater than in the control condition. This suggests that the bacteria produces more total acid in PEMF conditions.

Figure 18C:
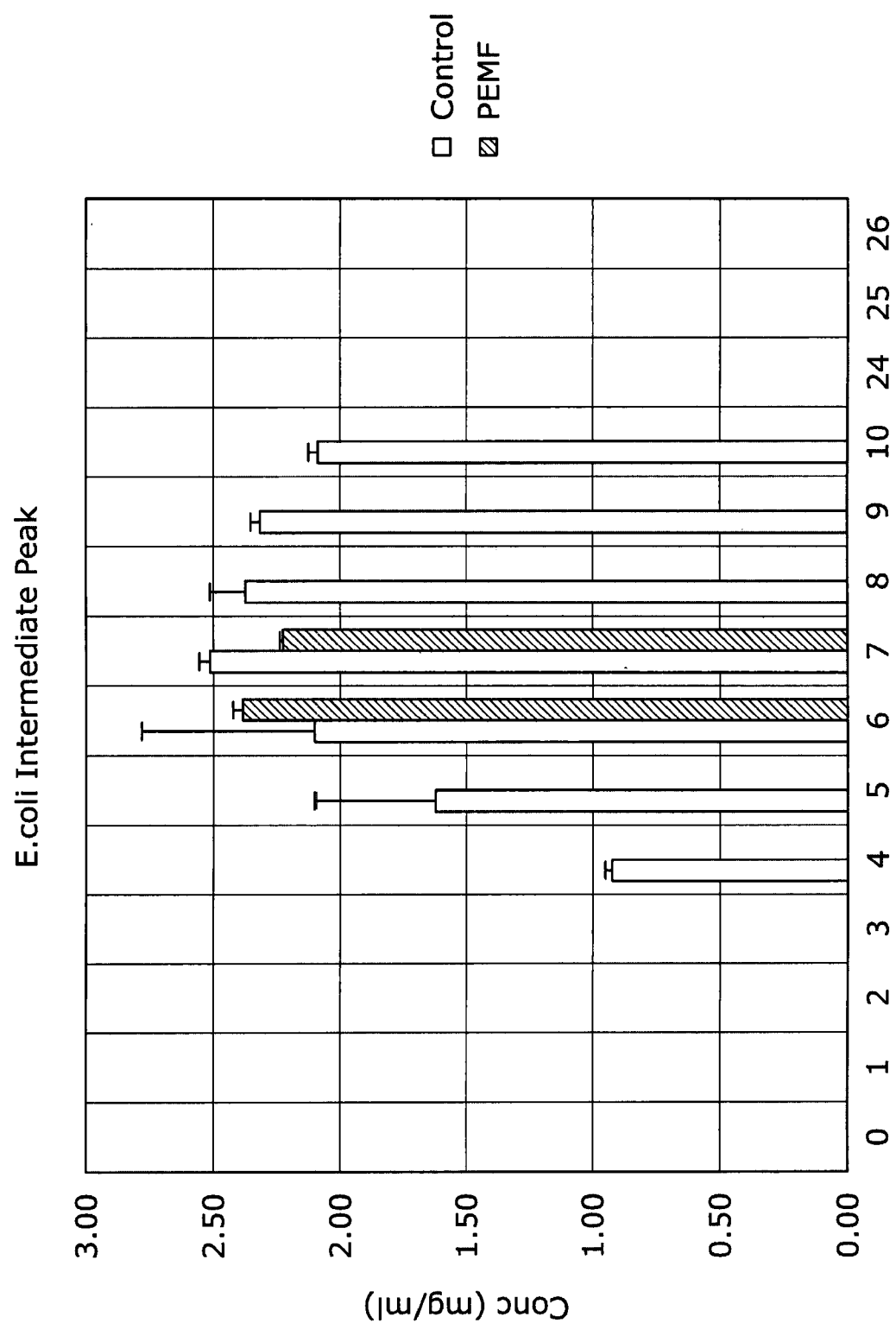
FIG. 18c illustrates metabolic intermediates in *E. coli*.
Figure 19A:
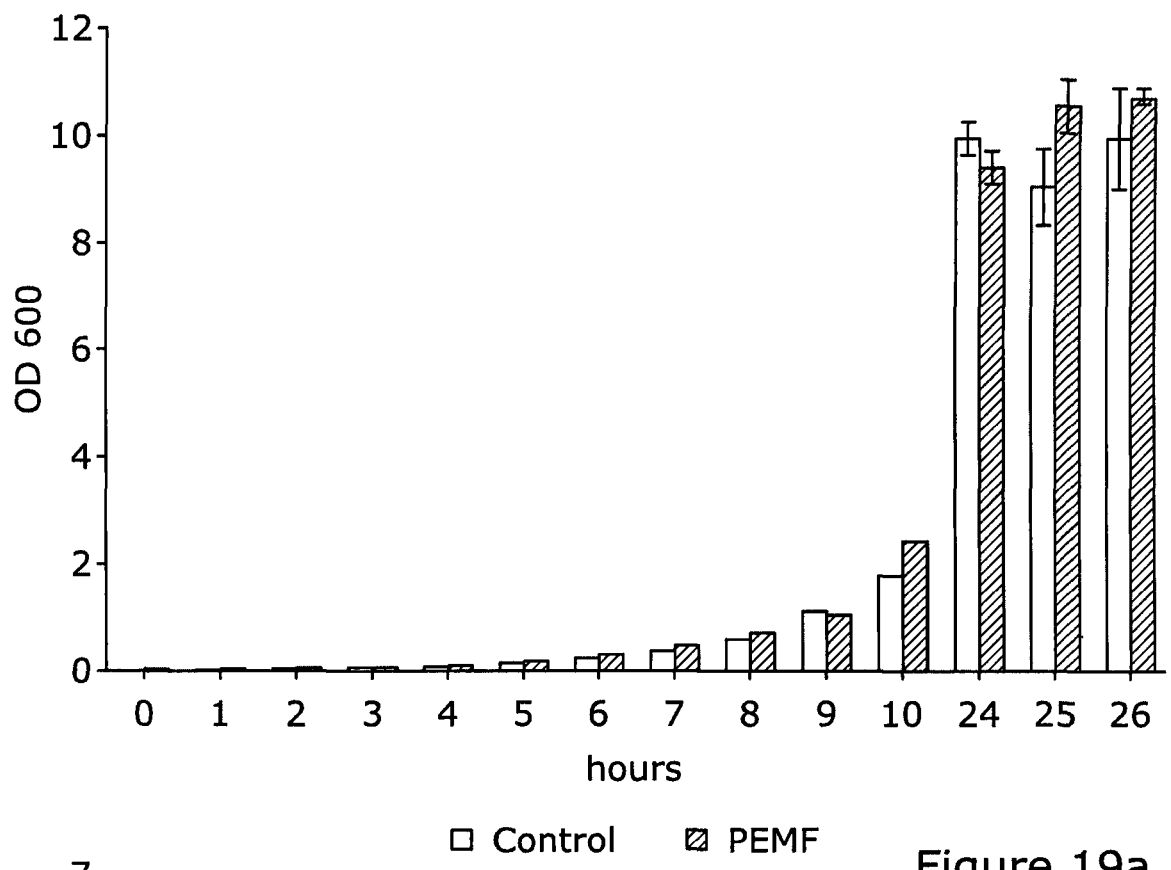
FIGS. 19a and 19b illustrate graphically a comparison of a control quantity of *S. cerevisiae* and the same material treated using PEMF in relation to optical density and DCW respectively.
Figure 19B:
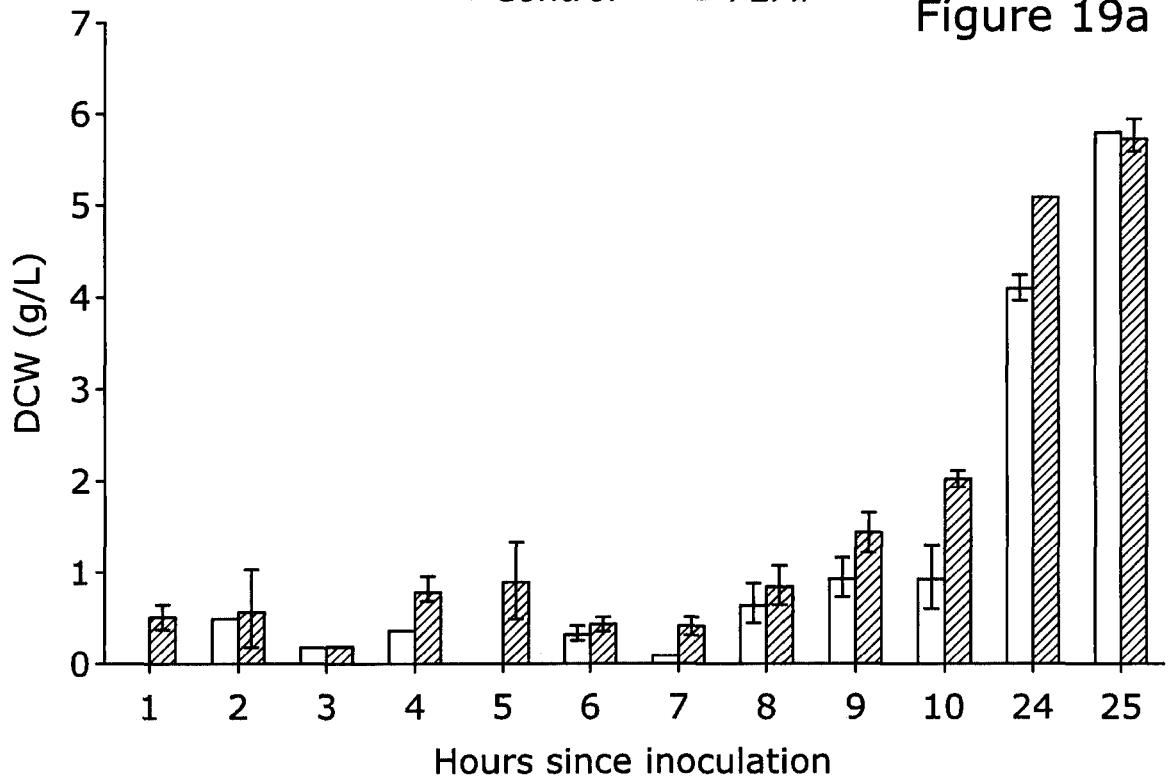

FIG. 18c then for the control *E. coli* material there is produced an unidentified metabolic intermediate throughout log phase growth which has gone by late stationary phase. However for the material exposed to the PEMF this intermediate only appears for a brief period during log phase before being consumed. This suggests that fermentation in PEMF conditions does not require short-term energy storage in the form of intermediates.

The *E. coli* is a strain that expresses two organic acids, acetic and formic, so the organism is clearly expressing more of these compounds, ca 15%. The differences are statistically significant. Clearly if this increased expression is repeated in a strain engineered to produce pharmaceuticals advantageous benefits can be obtained.

Referring now to FIGS. 19a-25, the same tests as with regard to FIGS. 15-18c were undertaken but in this case in relation to the yeast *S. cerevisiae* material. With regard to these results, the material which was exposed to PEMF grew faster than the control quantity and also entered the exponential phase of growth earlier than in the control quantity. After a lag phase of 5 hours, the fermentations exposed to PEMF entered the exponential phase after 6 hours of incubation. Indeed, higher OD values and DCW values were recorded starting from this point. While the final cell concentrations after 25 hours of incubation of the control and PEMF exposed materials were equivalent and could mean that the controlled fermentation eventually caught up with the material under PEMF stimulus, these results do show that a faster throughput is possible using the PEMF exposure to achieve at least the same level of fermentation more quickly than the material which is not exposed to PEMF.

Figure 20:
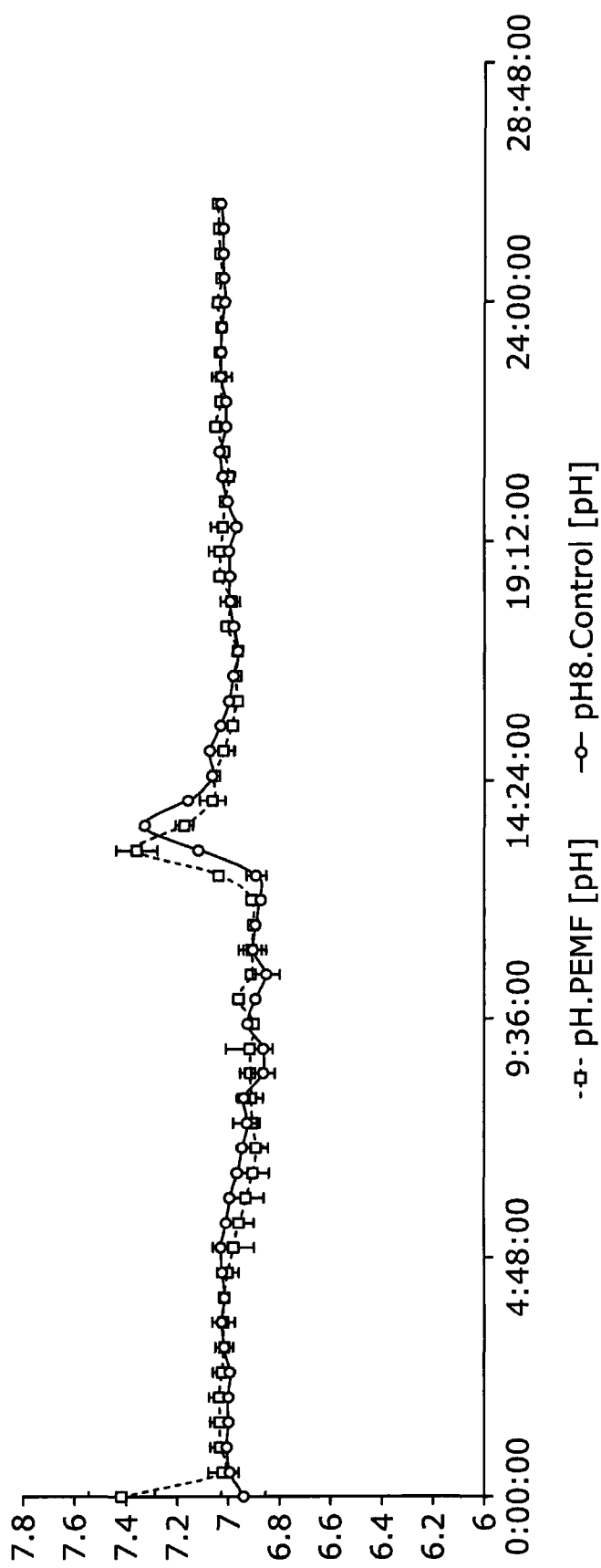
FIG. 20 illustrates graphically a comparison of a control quantity of *S cerevisiae* and the same material treated using PEMF with respect to pH over time.

With regard to the pH value, shown in FIG. 20, then in the PEMF fermentations, the acidifying activity of the culture is started between 30 minutes to 1 hour earlier than for the material in the control. Again, therefore, there may be potential advantages of a faster throughput of the fermentation.

Figure 21:
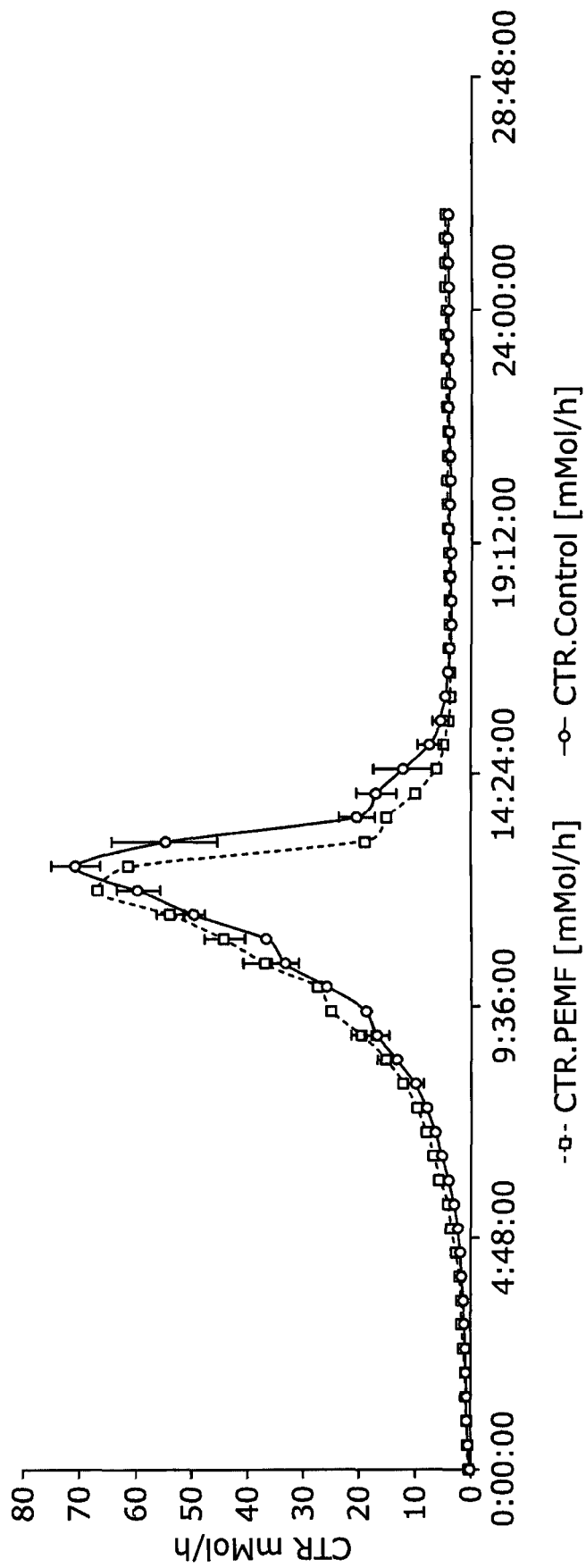
FIG. 21 illustrates graphically a comparison of a control quantity of *S. cerevisiae* and the same material treated using PEMF with respect to cell respiration over time.

With regard to FIG. 21 and cell respiration, the CEO transfer ratio (CTR) showed that while the overall maximum cell respiration was reached sooner under PEMF stimulus, which may be due to the cells entering the expediential phase of growth earlier, there was no significant difference in the overall cell respiration. Thus, in conclusion, with regard to FIGS. 19a-21, it is shown that faster throughput rates can e achieved without adversely affecting the final levels of fermentation which are achieved. As a result, in one use, the yeast will produce a greater amount of ethanol in a shorter time, thereby providing increased productivity rates on a commercial and industrial basis.

Figure 22:
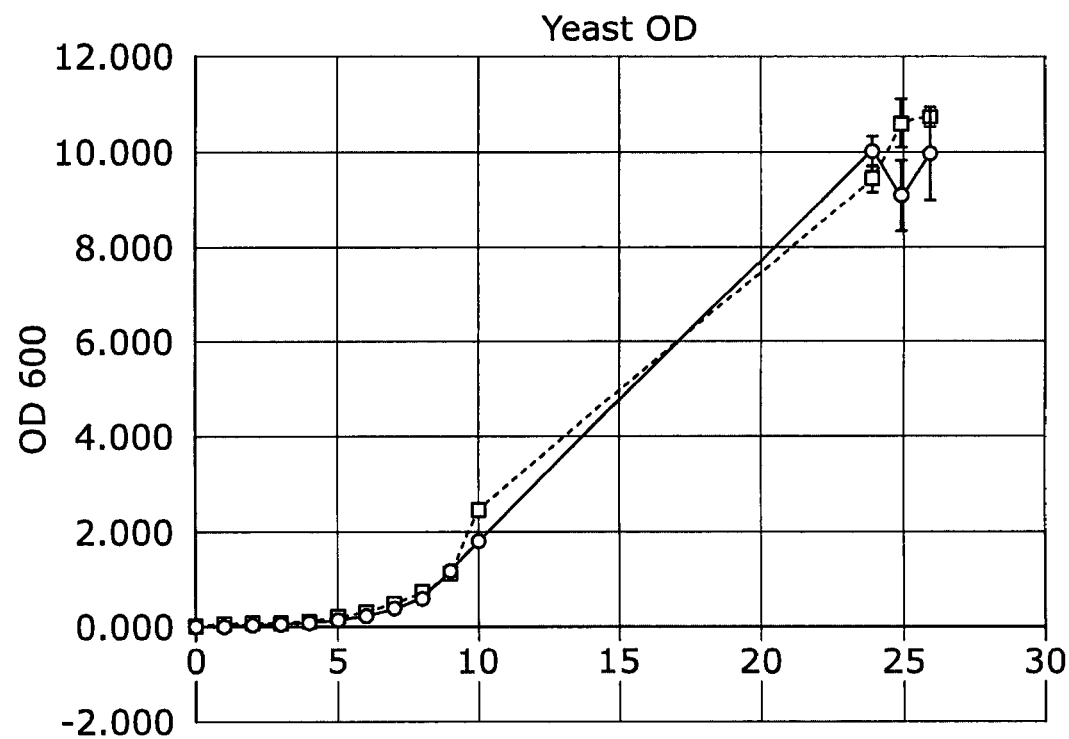
FIGS. 22 and 23a and 23b illustrate metabolic activity in *S. cerevisiae*.
Figure 22:
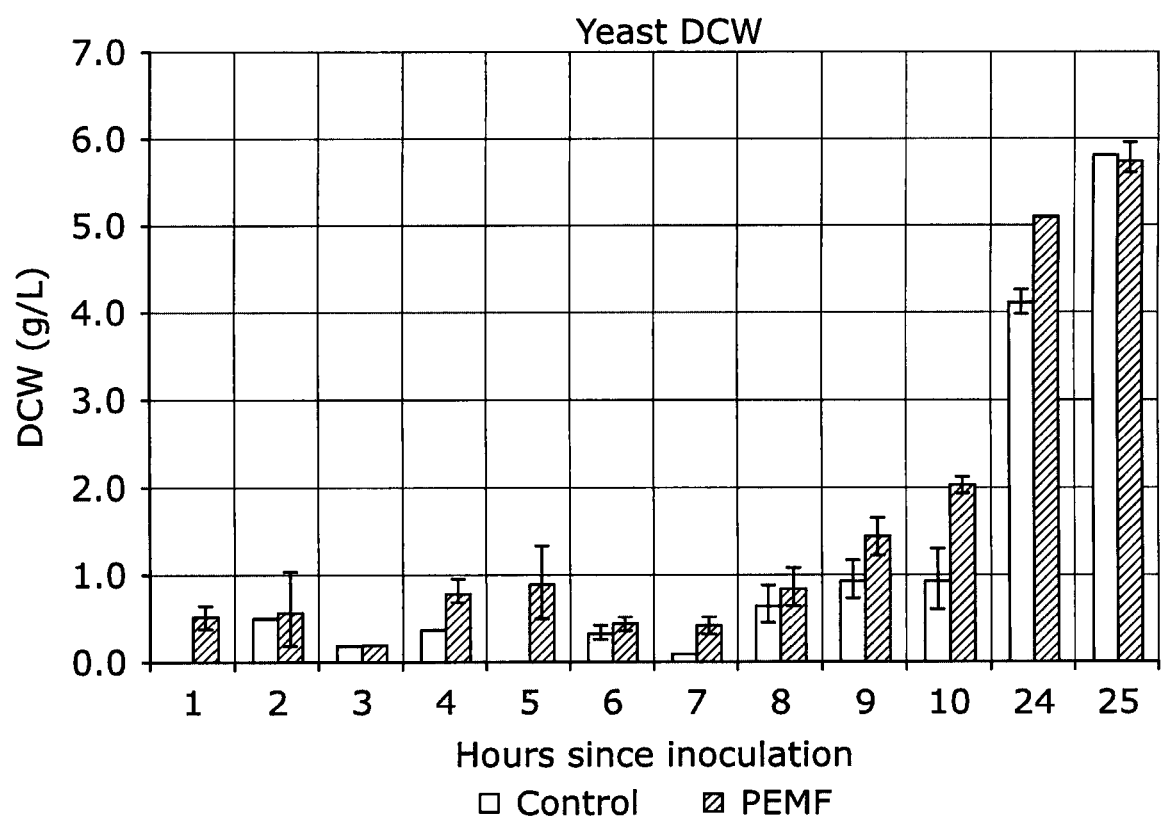
Figure 23A:
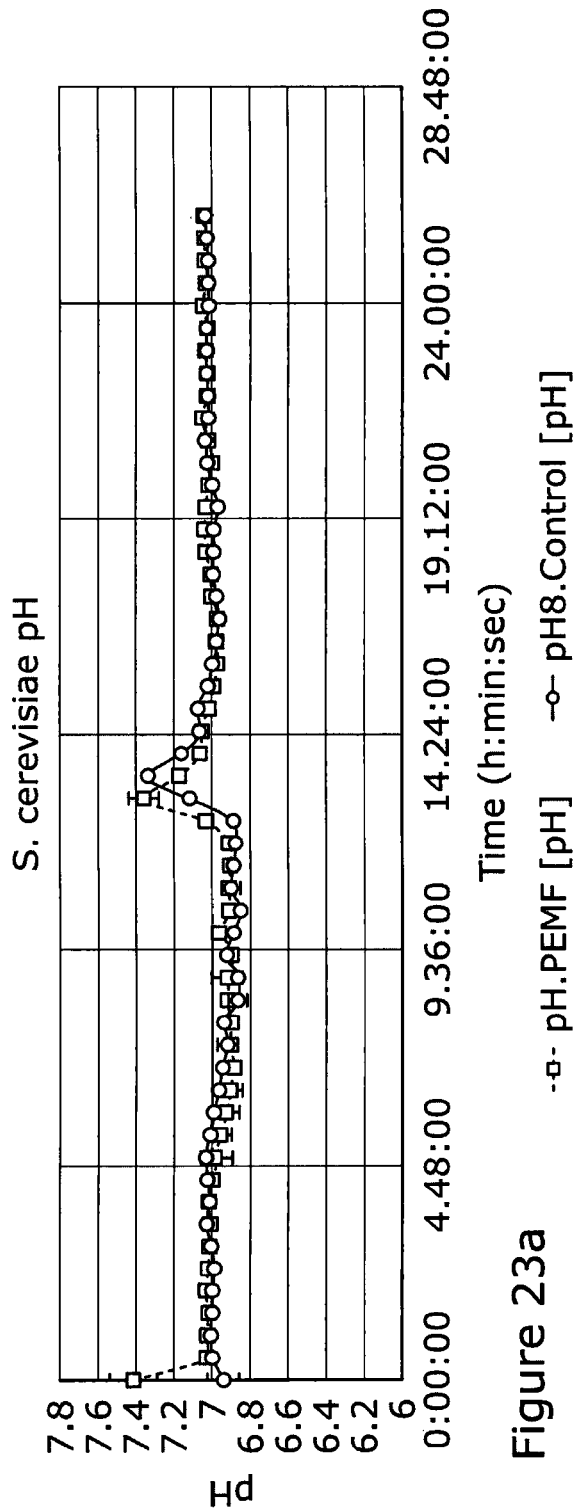
Figure 23B:
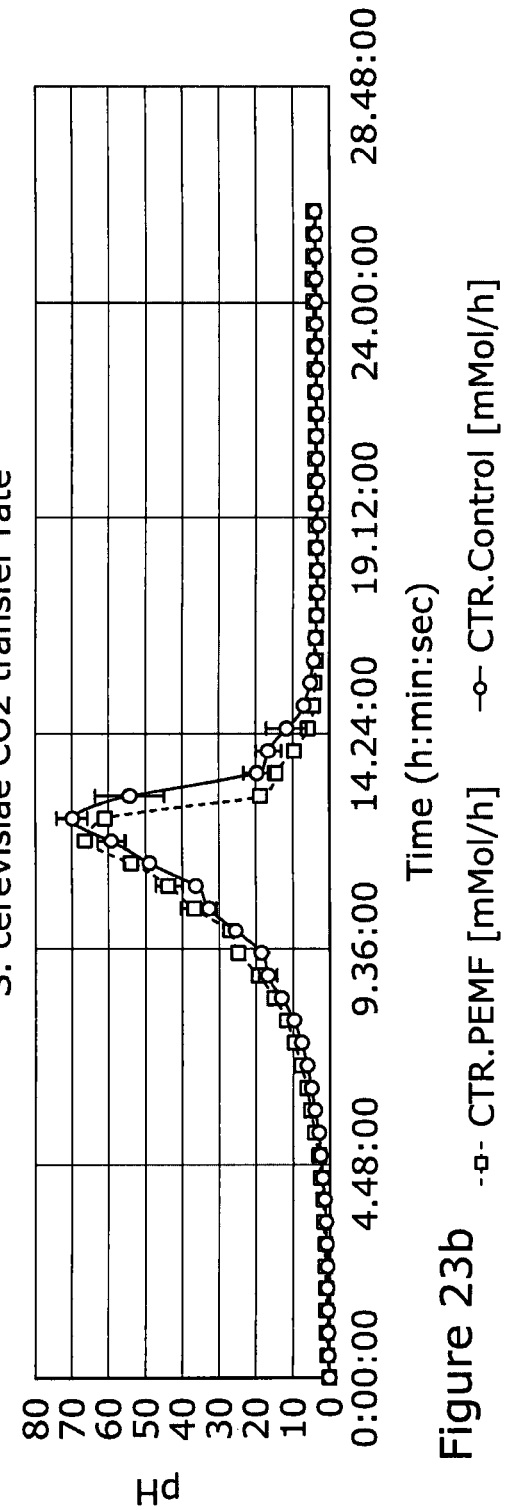

FIGS. 22 and 23a and b, illustrate that in PEMF conditions the rate of growth, respiration and acid production in *S. cerevisiae* increases earlier than in control conditions. This suggests that *S. cerevisiae* reaches log phase, and hence production phase, earlier in PEMF conditions.

The considerable differences in the fermentation which is achieved from the treatment using PEMF is shown to produce higher concentrations of alcohol and it is believed that in certain instances the maximum alcohol production from the material is reached at an earlier stage in the fermentation process than with the material which is not exposed to the PEMF.

Figure 24:
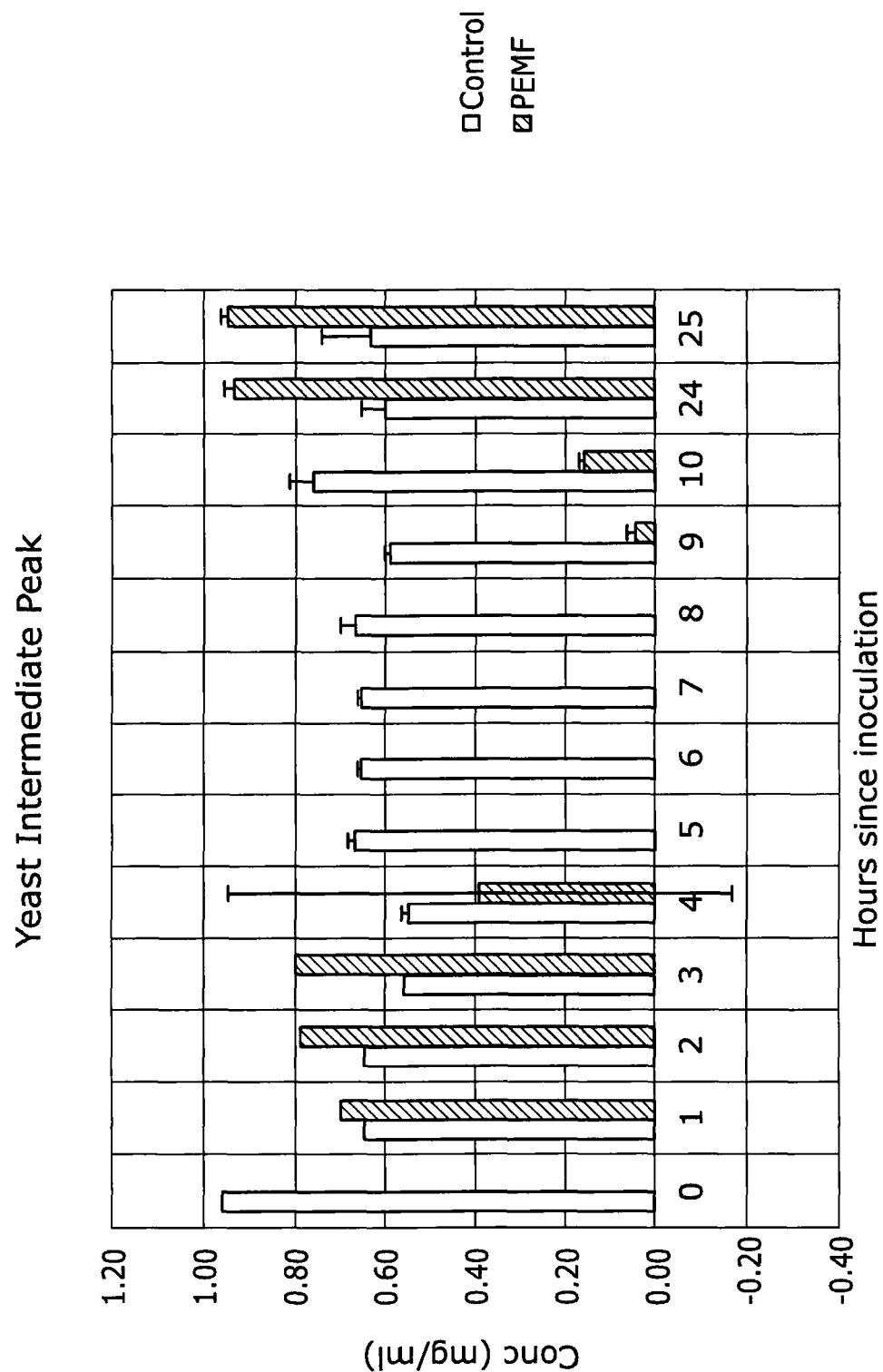
FIG. 24 illustrates metabolic intermediates in *S. cerevisiae*.

With regard to FIG. 24 there is illustrated that for the control material and conditions the *S. cerevisiae* culture contains a fairly constant amount of an unidentified metabolic intermediate throughout the fermentation process. However for the material exposed to PEMF conditions this intermediate completely disappears in early log phase, only to reappear later in log phase suggesting it is use up in some way but then produced again.

Figure 25:
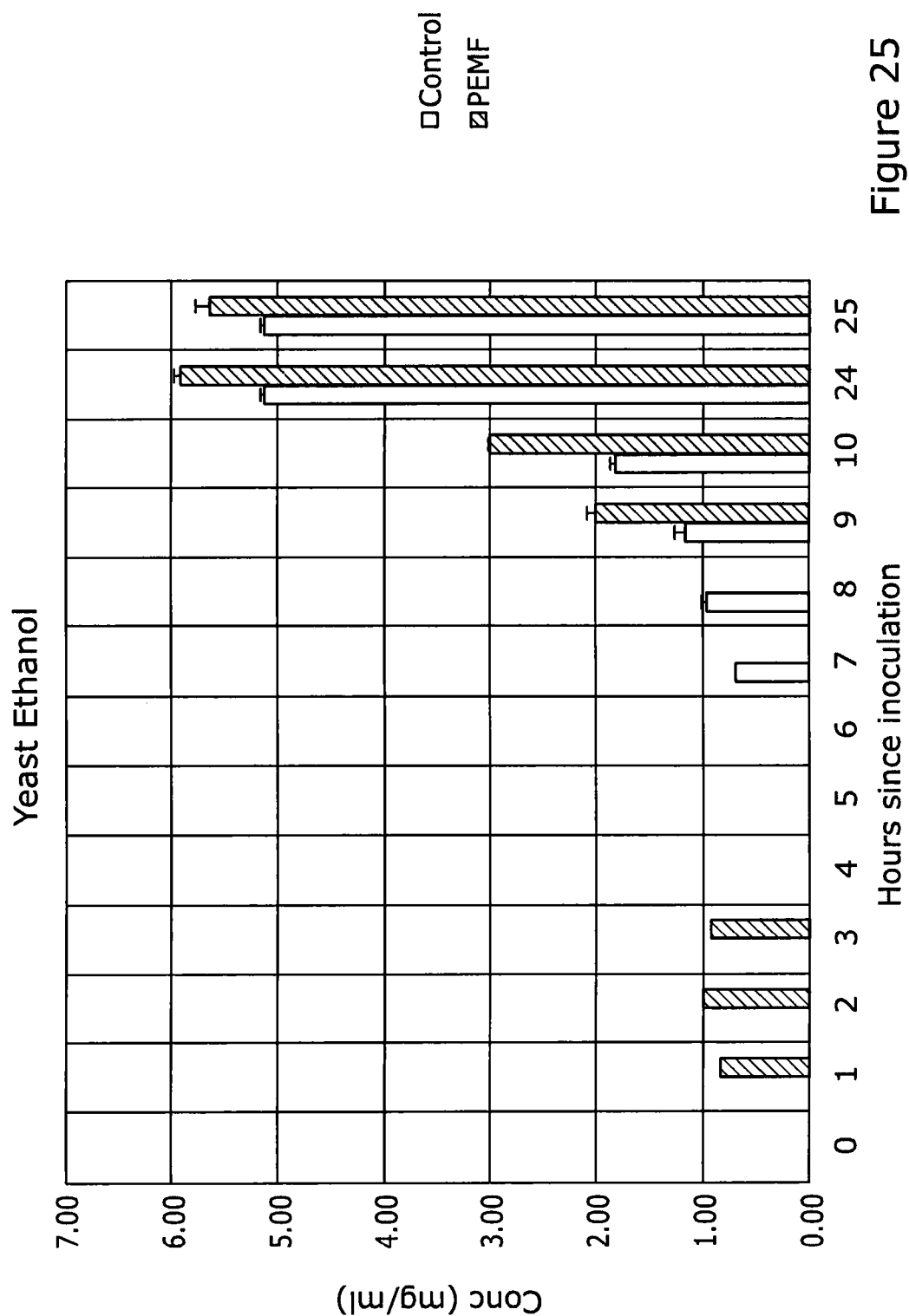
FIG. 25 illustrates ethanol production in *S. cerevisiae*.

With regard to FIG. 25 there is illustrated the exposure of the material to PEMF and it is shown that the same beings producing ethanol much later in the fermentation than the control material. However the concentration of ethanol in later stages of fermentation is higher in the material which is exposed to PEMF conditions, despite the delay in production and this suggests that the use of PEMF has a substantial effect on alcoholic production in this strain.

It should be appreciated that while the results are from tests performed in relation to *E. coli* and *cerevisiae*, other cultures could be used such as for example mammalian cell cultures. As mammalian cell cultures are fully aerobic then it is believed that results from these cultures will be equally as inventive and novel as those disclosed about if not more so.

In summary therefore the test results show surprisingly beneficial data from *E. coli* in terms of 57% more weight of culture produced by the application PEFM system, 74% more metabolic activity in *E. coli* by comparison to the control quantity. With regard to the yeast there is a much earlier entry into the exponential phase for the material treated using PEFM with the potential to reduce overall batch cycle time in Bioethanol production.

In this embodiment the apparatus and method in accordance with the invention is particularly effective under aerobic conditions, which is where the yeast is before it starts producing alcohol and the E. coli is under constant aerobic conditions. This has potentially major advantages for pharmaceutical production since many bio-drugs are expressed out of E. coli.

As such, the use of the PEMF technology increases metabolic activity in Escherichia coli, increases the alcohol production rate in Sacchoromyces cerevisiae and advantageously affects the production of metabolic intermediates in E. coli and S. cerevisiae.

A further embodiment and example of use of the invention is the use of pulsed electromagnetic field (PEMF) patterns on mammalian cell cultures. In accordance with the invention the PEMF technology was used in conjunction with glass stirred tank bioreactors to produce an IgG subclass 2 (IgG2) from an IgG expressing hybridoma cell line which had previously been grown in traditional cell culture flasks and STR, with an IgG yield in the region of 30-50 μg/mL and 130 μg/mL, respectively, after dialysis and concentrating.

The aim of the tests was to assess whether PEMF has an impact on mammalian cell metabolism, in particular with respect to increasing IgG production and to assess whether the cultivation in STR of an IgG expressing cell line could lead to a competitive IgG yield (target of 300-500 μg/mL) and two separate experiments were performed:

1. The objective of the first experiment was to carry out quadruplicate benchtop 1 L cell cultures, grown without any surrounding PEMF (negative control experiment). During this experiment, a set of parameters to grow the cell line in STR was determined using the literature review, equipment supplier advice, a test run, and internal knowledge on the cell line.
2. The objective of the second experiment was to carry out quadruplicate benchtop 1 L cell cultures, grown in the presence of the PEMF (test experiment). During this experiment, the same set of parameters were used again as pre-determined in objective 1, regardless of the yield reached previously.

In the protocol the following parameters were used:
1. pH-control using 7.5% sodium bicarbonate as well as CO2 to maintain a pH between 7 & 8.
2. Gas flow rate set at 3 L/h to minimise flow rate deviation of bioreactors and improve the repeatability of the experiment.
3. Implementing four PEMF modules each attached directly to one of the four bioreactors during the PEMF run.
4. DO control using air to maintain a minimum dissolved oxygen concentration of 40%.

In the tests the PEMF apparatus configuration was four modules that emit a unique PEMF pattern. For the control condition, no PEMF apparatus was used and all other PEMF/Bluetooth devices were switched off and removed from the lab throughout the cell culture. For the experimental condition each of the four PEMF apparatus modules were placed in direct contact with one of the glass stirred tank bioreactor (STR), switched on, and kept on throughout the cell cultures, whilst all other PEMF/Bluetooth devices were kept out of the lab. The cell cultures were monitored using online gas analysers, online and offline pH monitoring, offline cell count measurements and HPLC analysis of IgG production. The murine hybridoma cell line and media were provided pre-mixed in 1 L sterile bottles by The Antibody Company. The media was composed of Dulbecco's Modified Eagle's Medium (DMEM, Life Technologies) with GlutaMAX™ (Life Technologies) and low-IgG foetal bovine serum (FBS) (Life Technologies). Pluronic F-68 (Life Technologies) was added at a 1:100 dilution to reduce foaming in the reactors. See appendix for further information on media composition.

Prior to each set of cell cultures, the DASGIP reactors were autoclaved the day prior to inoculation. The reactors were stored in a laminar flow hood overnight with periodic UV light treatment to maintain sterility.

Control run: The pre-culture of the murine hybridoma cells were prepared by The Antibody Company and split into 4×1 L bottles of media (as described above) at a concentration of $3.5 \times 10^5$ cells/mL with cell viability of 64.8%.

PEMF run: The pre-culture of the murine hybridoma cells was split into 4×1 L bottles of media (as described above) at a concentration of $4.87 \times 10^5$ cells/mL with cell viability of 77%.

These were immediately transported to FlexBio where 1 L of pre-culture was placed into each reactor of the Eppendorf DASGIP Parallel Bioreactor system, equipped with pitched-blade impellers.

TABLE 1

The conditions used in the control of the 4 reactors in each run.

| Parameter | Condition |
|---|---|
| pH | 7.4 (controlled with sparging $CO_2$ and 7.5% sodium bicarbonate) |
| Agitation | 100 rpm |
| Airflow | 3 L/h |
| Temperature | 37° C. |
| Antifoam | 100 μL/L |
| Dissolved oxygen | 40% (controlled with sparging air) |

A 7 mL sample was taken from each fermenter at the sample points specified in Table 2.

TABLE 2

The time from the end of inoculation to the start of each sample point discussed in this report. Sample times are rounded to the nearest day throughout the results section.

| | Time since inoculation (days, hours) | |
|---|---|---|
| Sample number | Control | PEMF |
| Inoculation | 0 d, 0 h, 0 m | 0 d, 0 h, 0 m |
| 1 | 0 d, 1 h, 35 m | 0 d, 1 h, 55 m |
| 2 | 0 d, 23 h, 11 m | 0 d, 22 h, 42 m |
| 3 | 1 d, 21 h, 35 m | 1 d, 21 h, 45 m |
| 4 | 3 d, 0 h, 45 m | 3 d, 1 h, 19 m |
| 5 | 4 d, 1 h, 0 m | 4 d, 1 h, 16 m |
| 6 | 4 d, 22 h, 0 m | 4 d, 21 h, 56 m |
| 7 | 5 d, 23 h, 23 m | 5 d, 23 h, 22 m |
| Harvest | 5 d, 23 h, 38 m | 6 d, 00 h, 00 m |

For the cell cultures using Pulsar Technology, the four PEMF devices were set up by attaching one device to each of the four glass DASGIP reactors and switched on. They remained switched on and plugged in throughout the cell culture run. Unfortunately, one bioreactor was terminated due to a fault in the operation setting.

The following parameters were analysed:

Offline pH was measured using a HANNA HI8424 pH meter (Hanna Instruments).

2 mL of sample was transferred to a 15 mL falcon tube and the probe inserted into the tube below the liquid line. This was done within 2 minutes of removing the sample from the reactor to reduce rapid CO2 degassing, thus affecting the pH of the sample.

Growth rate was measured by using from the remaining unfiltered sample, 50 µL was transferred to an Eppendorf containing 50 µL of Trypan Blue (Sigma Aldrich).

The sample was mixed with the stain by gently pipetting up and down. The stained sample was applied to a cell counter slide (Nexcelom Bioscience) and the cells were counted using an automated Nexcelom Cellometer (Nexcelom Bioscience).

From this procedure the following information was recorded:

Total cell count (cells/mL)
Live cell count (cells/mL).
Ratio of live/dead cells
Average cell diameter (µm)
Viability (%)

Glucose concentration was measured by using the remainder of the sample which was filtered at 0.22 µm to remove all cells and a commercially available glucose meter (Accu-Chek Mobile) following the manufacturer's instructions in which 10 µL of filtered sample was transferred onto the strip and the displayed value recorded.

Monoclonal antibody concentration was measured by storing a quantity of the sample at −20° C. and later thawed under sterile conditions.

To determine IgG concentration, supernatant samples were analysed using ion exclusion chromatography.

HPLC: Agilent 1290 Infinity.
Column: Thermofisher Scientific Poros A20. Buffer A: 50 mM phosphate, 150 mM NaCl.
Buffer B: 12 mM hydrochloric acid, 150 mM NaCl.
Elution: Gradient elution (Table 3)
Injection volume: 20 µL.
Measurement: Absorbance at 280 nm and 214 nm.
Standard 2: Normal Mouse IgG (Sigma Aldrich, 12-371) (standard curve generated)

TABLE 3

Summary of the gradient elution used for the IgG analysis.

| Time (min) | % B | Flow (mL/min) |
|---|---|---|
| 0.00 | 0 | 2.5 |
| 4.50 | 0 | 2.5 |
| 4.51 | 100 | 2.5 |
| 7.50 | 100 | 2.5 |
| 7.51 | 0 | 2.5 |
| 15.00 | 0 | 2.5 |

Statistical Analysis

Graph production, data distribution, and statistical analysis were performed using Microsoft Excel (2016). Student t-tests were used to analyse experiments comparing independent sample data. Statistical significance was achieved if $P<0.05$. All statistical analysis was carried out using data obtained from four independent biological replicates for the control group (n=4) and three independent biological replicates for the treatment group (n=3). Error bars depict the standard deviation of the sample group An analysis of the results reveals that with regard to growth rates and metabolic activity the average total cell count of the cell cultures exposed to PEMF was higher than the average recorded when the cells were cultured without the PEMF device (control cultures) (FIG. 30). There was a significant difference (p=0.048) between the PEMF-treated and untreated cells after 4 days of growth (FIG. 30). The control bioreactors reached a maximum average total cell count of $1.44 \times 10^6$ cells/mL 6 days after inoculation, compared to an average total cell count of $6.06 \times 10^6$ cells/mL reached by the PEMF-exposed culture (FIG. 30). After 4 days of growth, the average total cell number in the treated culture remained higher than the control, but no significant difference was recorded (p>0.35) (FIG. 30).

The average number of total live cells in the PEMF-exposed culture was higher compared to the control culture from day 0 to day 2, although this difference was not significant (p>0.122). After 3 days of growth, there was a significantly higher number of live cells in the PEMF-treated culture compared to the control culture (p=0.009) (FIG. 30). After 3 days of growth, the average total live cell number decreased in the PEMF-exposed culture, whereas the number of live cells continued to increase slightly in the control culture (FIG. 30).

In both runs, glucose consumption followed the same pattern, with glucose consumed rapidly 1 to 3 days after inoculation, and then remaining relatively constant until harvest (FIG. 31). Although not considered significant (p>0.05), the glucose concentration in the PEMF-treated cells was consistently lower than the glucose concentration in the control culture from days 1 to 3 (FIG. 31).

The lower concentration of glucose in the PEMF-treated cell media could suggest a higher rate of glucose consumption in this culture compared to the control culture, which could be directly related to the higher cell count observed for the PEMF-exposed cells, as mentioned above (FIG. 30). Therefore, we could hypothesise that the PEMF induced a higher rate of glucose consumption which could be indicative of a higher rate of cellular respiration (needed for cell division). However further studies would have to be carried out to determine whether this assumption is correct The results of a previous study (ECO-410) indicated that stricter pH control was essential to counteract the effect of lactic acid production on the acidity of the cell culture media. During the present study, the pH of the cultures was controlled using $CO_2$ and 7.5% sodium bicarbonate to ensure that the pH stayed within a range of 7.3-7.8. (FIG. 32). The pH of both the PEMF-treated and untreated cultures remained fairly stable throughout the experimental runs as shown in FIG. 32.

Oxygen uptake in the PEMF-exposed cells occurred at a slightly faster rate compared to the control, with the PEMF-exposed cultures reaching their minimum % dissolved oxygen (10.5%) within 3 days, compared to the control cultures which reached their minimum % dissolved oxygen (6.7%) within 3.5 days (FIG. 33). As discussed in the previous study, during aerobic respiration (in the presence of oxygen) glucose is catabolised and dissolved oxygen is taken up from the media, for utilisation in the electron transport chain, to produce ATP. As the cells enter their exponential phase, they divide rapidly, producing and utilising lots of ATP. When oxygen levels are too low, the cells switch from oxidative phosphorylation to lactic acid fermentation and cell division stops while % Dissolved Oxygen (DO) rises again. In the present study, the consumption of dissolved oxygen was the sharpest for the PEMF exposed cells up to day 3, as it was for glucose consumption and total cell count (FIGS. 30,31, 33). Thus, taken collectively, the data seems to suggest that higher cellular metabolic activity was indeed induced by the PEMF.

Airflow during the cell culture runs increased at a higher rate in the PEMF-exposed cultures compared to the control cultures, reaching its maximum flow rate (3 sL/h) within approximately 2 days of growth compared to 2.5 days of growth, respectively (FIG. 33). The decrease in % dissolved oxygen during both experimental runs suggests that the cells were taking up oxygen at a faster rate than it could be introduced into the media (FIG. 33).

Maintaining a total gas flow rate of 3 sL/h throughout the run enabled more air to be pumped into the system.

The DASGIP bioreactor system enables up to three different gases (or gas compositions) to be introduced to each of the four bioreactors for the duration of an experimental run. During this study, the three separate gases were carbon dioxide (CO2), nitrogen (N2) and an air mix (approximately 21% oxygen, 78% nitrogen, 0.04% CO2). The gas flow rate was set to 3 sL/h, which meant that the combined flow rate of all three gases had to always equal 3 sL/h, illustrated as 'total maximum flow rate' in FIG. 34. In this study, nitrogen was utilised as an inert gas to maintain the desired gas flow rate (FIG. 34). At the beginning of the experimental run, the cells were utilising oxygen from the media at a low rate, therefore the ratio of air to N2 into the system was fairly equal (FIG. 34). As the run continued, and the oxygen requirements of the culture increased, the ratio of air in total gas mix increased to the maximum limit (3 sL/h), with a small volume allocated for CO2 for pH control and almost no N2 (FIG. 34). As the cells entered anaerobic respiration, the glucose concentration depleted and the cells stopped dividing and switch to an anaerobic fermentation metabolism. As explained above, the need for O2 decreased, and leading to the volume of air into the system to decrease. This was compensated by increasing the volume of nitrogen to ensure that the total gas flow rate remained close to 3 sL/h (FIG. 34).

The beginning of base addition occurred earlier in the PEMF-treated cultures compared to the control cultures, approximately 57.5 hours (2.5 days) after inoculation compared to approximately 68 hours (3 days), respectively (FIG. 35). More base was added to the PEMF-treated cells compared to the untreated cells, 15.2 mL compared to 14.2 mL, respectively (FIG. 35). The earlier addition and higher total volume of base strongly suggest that the cells in the PEMF-exposed cultures were producing lactic acid earlier in the cell culture run and at a higher concentration compared to the control cultures. Consistent with the higher rate of oxygen uptake and glucose consumption, this could be indicative of the cells within the PEMF-exposed cultures utilising oxygen at a faster rate and entering lactic acid fermentation before the cells within the control cultures (FIGS. 31, 33 & 35).

On the basis that PEMF maximises metabolism as discussed above, while glucose uptake was maximised during the first phase of growth, lactic acid production was also ultimately maximised during PEMF exposure condition. Indeed, under electromagnetic field biostimulation in a pH-controlled environment, the cells may produce a higher concentration of lactic acid (a by-product compound produced during anaerobic condition) as was the case with the *S. cerevisiae* (also a eukaryotic cell) where ethanol production (also a by-product from anaerobic fermentation) was +20% higher when the cells were exposed to PEMF.

The total cell density of hybridoma cells was shown to be higher in the PEMF exposed cultures when compared to the control cultures, during the first phase of growth (from inoculation up until glucose depletion). Live cell count was also found to be greater in the PEMF treated cultures over the same period. Glucose metabolism rate was also increased in cells exposed to PEMF which can indicate that the PEMF apparatus and the use of the same positively impacts the growth and metabolism of murine hybridoma cells by stimulating and maximising nutrients uptake.

In both control and PEMF exposed cells, cells are multiplying during exponential growth thus requiring a higher oxygen demand, which was observed in a drop in DO levels. Specifically, the PEMF exposed cells showed a stronger and faster growth which was supported with higher glucose uptake. This led to reaching oxygen-limiting condition earlier than the control cells and thus triggering lactic acid production earlier as well. It also appeared that the PEMF exposed cells, in pH 7.4 controlled environment, were able to produce a higher concentration of lactic acid (indirectly observed by a higher base addition) than the control cultures. Lactic acid being inhibitory to IgG production, lower level of IgG were recorded for the PEMF exposed cells.

DO control is a factor to ensure the highest rate of growth for the cell culture of murine hybridoma in stirred bioreactors and prevent triggering lactic acid production. Additionally, this experiment also raised the possibility that PEMF stimulates the production of lactic acid, in the same way, it stimulates the consumption of glucose (as a similar phenomenon was observed before with *S. cerevisiae*). Dissolved oxygen levels should remain constant and high (DO>40%). To achieve this, for this particular cell line, it is recommended to increase the gas flow rate from 0.05 vvm to 0.1 vvm (6 L/h for a 1 L working volume) and/or to use solely pure oxygen compressed gas instead of compressed air as an oxygen supply gas. This should ensure that a high level of oxygen is maintained throughout the cell culture and should prevent the production of lactic acid.

It is therefore shown that with regard to the use of the method and apparatus in relation to mammalian cell culture the use of the modules to generate the PEMF in relation to the product over a three day period provoked an increased metabolic rate as seen by the accelerated cell growth which was 27% higher at Day 3 whilst maintaining the concentration and yield of IgG which is of significant benefit as all cells and conditions are identical other than the use of the PEMF and thereby illustrates the use of the method and apparatus in accordance with the invention provokes greater metabolic activity as shown by increased expression level per cell and increases cell metabolism by significant acceleration of cell division in the vicinity of 30% and shows a significant increase in cellular expression of IgG in the vicinity of 25% so that overall there is a productivity gain of potentially 60+% (30% more cells producing 25% more per cell).

The invention claimed is:

1. A system to allow application of a pulsed electromagnetic wave to a cell culture for a period of time, to alter a condition of the cell culture, said system comprising:
   a signal generator configured to generate the pulsed electromagnetic wave;
   a controller comprising a control circuit or processor configured to control generation of the pulsed electromagnetic wave;
   a container in which the cell culture is located; and
   at least one support that includes one or more modules, wherein each module of the one or more modules comprises a transmitter and an antenna arranged for transmission of the pulsed electromagnetic wave towards the container, and said at least one support includes or is connected to said controller, and the at least one support is positioned in proximity to the container so as to allow the cell culture to be exposed to the pulsed electromagnetic wave which is generated; and wherein the altered condition of the cell culture is a change of metabolic productivity and/or production rate of the cell culture.

2. The system according to claim 1, wherein the controller is configured to control frequency and pulse sequence of the pulsed electromagnetic wave.

3. The system according to claim 1, wherein the one or more modules comprise a plurality of the modules provided in a fixed array or configuration on the at least one support.

4. The system according to claim 1, wherein the container has walls and the at least one support is located externally of the container and the pulsed electromagnetic wave is applied to the cell culture through one or more of the walls of the container in which the cell culture is located.

5. The system according to claim 1, wherein at least a part of the at least one support is located inside the container or the container has walls and the one or more modules is located within the walls of the container.

6. The system according to claim 1, wherein the at least one support comprises a plurality of supports that each include the one or more modules, wherein each of the plurality of supports is located at a different locations in proximity to the container, in order to provide the cell culture with a uniform exposure to the pulsed electromagnetic wave.

7. The system according to claim 1, wherein the transmitter is configured to transmit pulsed electromagnetic waves within an industrial, scientific, and medical (ISM) short-range radio frequency band.

8. The system according to claim 1, wherein the transmitter is configured to transmit pulsed electromagnetic waves with a frequency of 2.4 GHz.

9. The system according to claim 1, wherein the transmitter is configured to transmit the pulsed electromagnetic wave up to a distance of 15 metres.

10. The system according to claim 1, wherein the controller is configured to provide the pulsed electromagnetic wave in pulses which are in a range of 0.5-1.5 ms in duration.

11. The system according to claim 1, wherein the controller is configured to provide the pulsed electromagnetic wave in pulses that are each spaced apart by a rest period in a range of 40-66 ms.

12. The system according to claim 1, wherein the controller is configured to provide pulsed electromagnetic wave pulses within a range of 12-20 pulses per second.

13. The system according to claim 1, wherein the one or more modules are omnidirectional in terms of direction of emission of the pulsed electromagnetic wave in an omnidirectional manner to the cell culture.

14. The system according to claim 1, wherein the pulsed electromagnetic wave comprises pulses in which transmission power is in the order of microwatts.

15. The system according to claim 1, wherein the at least one support includes a housing that is transmissive to radio frequency electromagnetic waves, wherein the housing comprises the one or more modules, and wherein the transmitter is configured to transmit electromagnetic waves in a radio frequency band.

* * * * *